United States Patent
Kim et al.

(10) Patent No.: US 10,070,982 B2
(45) Date of Patent: Sep. 11, 2018

(54) LINK ASSEMBLY, FRAME, AND WALKING ASSISTANCE ROBOT

(71) Applicant: Samsung Electronics Co., Ltd., Suwon-Si, Gyeonggi-Do (KR)

(72) Inventors: Yongjae Kim, Seoul (KR); Youn Baek Lee, Yongin-si (KR); Jongwon Lee, Uiwang-si (KR); Byungjune Choi, Gunpo-si (KR); Jeonghun Kim, Hwaseong-si (KR); Se-Gon Roh, Suwon-si (KR); Minhyung Lee, Anyang-si (KR); Hyun Do Choi, Yongin-si (KR); Sunggu Kwon, Yongin-si (KR); Youngdo Kwon, Yongin-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 851 days.

(21) Appl. No.: 14/599,804

(22) Filed: Jan. 19, 2015

(65) Prior Publication Data
US 2015/0272764 A1 Oct. 1, 2015

(30) Foreign Application Priority Data
Mar. 28, 2014 (KR) .................. 10-2014-0037080

(51) Int. Cl.
*A61F 2/60* (2006.01)
*A61F 5/01* (2006.01)
(Continued)

(52) U.S. Cl.
CPC ............ *A61F 5/0102* (2013.01); *A01D 34/90* (2013.01); *A61F 2/60* (2013.01); *A61F 2/68* (2013.01);
(Continued)

(58) Field of Classification Search
CPC ........ A61H 1/024; A61H 1/0244; A61H 3/00; A61H 1/02; A61H 2003/007;
(Continued)

(56) References Cited

U.S. PATENT DOCUMENTS 3,446,091 A    5/1969   Stocker
4,269,026 A *  5/1981   Bulle ................. A44C 5/105
                                                      59/82

(Continued)

FOREIGN PATENT DOCUMENTS

DE          4011769 A1    10/1990
DE     102006016910 A1    11/2006
(Continued)

OTHER PUBLICATIONS

Extended European Search Report dated Jan. 4, 2016 for Application No. EP 15157640.
Partial European Search Report dated Sep. 4, 2015 for Application No. EP 15 15 7640.
Japanese Office Action dated Jan. 23, 2018 for Japanese Patent Application No. 2015-015298.
(Continued)

*Primary Examiner* — David B Jones
(74) *Attorney, Agent, or Firm* — Harness, Dickey & Pierce, P.L.C.

(57) ABSTRACT

A frame configured of a plurality of links pivotally connected to one another is flexibly bent, and pins that connect the plurality of links that constitute the frame are inserted into and slide in a curve-shaped slot and a slot in a vertical direction so that, even though the frame is bent, the entire length of the frame is increased and ends of the frame can be moved along a straight line that is horizontal with respect to the ground.

22 Claims, 20 Drawing Sheets

(51) Int. Cl.
*A01D 34/90* (2006.01)
*B25J 9/00* (2006.01)
*A61F 2/68* (2006.01)
*A61H 1/02* (2006.01)
*A61F 5/32* (2006.01)
*A61H 3/00* (2006.01)

(52) U.S. Cl.
CPC .................. *A61F 5/01* (2013.01); *A61F 5/32* (2013.01); *A61H 1/02* (2013.01); *A61H 1/024* (2013.01); *A61H 1/0244* (2013.01); *A61H 3/00* (2013.01); *B25J 9/00* (2013.01); *A61F 2005/0141* (2013.01); *A61F 2220/0091* (2013.01); *A61H 2003/007* (2013.01); *A61H 2201/0192* (2013.01); *A61H 2201/1207* (2013.01); *A61H 2201/163* (2013.01); *A61H 2201/165* (2013.01); *A61H 2201/1642* (2013.01); *Y10T 74/20207* (2015.01)

(58) Field of Classification Search
CPC .... A61H 2201/0192; A61H 2201/1207; A61H 2201/163; A61H 2201/1642; A61H 2201/165; A61F 2/60; A61F 5/32; A61F 5/0102; A61F 5/01; A61F 2/68; A61F 2005/0141; A61F 2220/0091; B25J 9/00; B25J 9/15; A01D 34/90
USPC ............................................................ 59/78
See application file for complete search history.

(56) References Cited

U.S. PATENT DOCUMENTS

| | | | |
|---|---|---|---|
| 4,649,906 A | | 3/1987 | Spademan |
| 2006/0249929 A1* | | 11/2006 | Holzer ................ A63C 9/02 |
| | | | 280/611 |
| 2010/0076355 A1 | | 3/2010 | Ikeuchi et al. |
| 2011/0098618 A1 | | 4/2011 | Fleming |
| 2011/0172570 A1 | | 7/2011 | Shimizu et al. |
| 2012/0226203 A1 | | 9/2012 | Nakashima et al. |
| 2014/0005798 A1 | | 1/2014 | Bache et al. |

FOREIGN PATENT DOCUMENTS

| | | |
|---|---|---|
| EP | 0 910 441 B1 | 3/2003 |
| EP | 1760361 A1 | 3/2007 |
| EP | 2614807 A1 | 7/2013 |
| EP | 2898861 A1 | 7/2015 |
| JP | 2007-275482 A | 10/2007 |
| JP | 2011143211 A | 7/2011 |
| KR | 20130010609 A | 1/2013 |
| KR | 20130045777 A | 5/2013 |
| WO | WO-9738759 A1 | 10/1997 |

OTHER PUBLICATIONS

The State Intellectual Property Office of P.R. China First Office Action dated Feb. 24, 2018 for CN Application No. 201510142043.8 (with English translation).
Japanese Patent Office Decision of Patent dated Jul. 3, 2018 for corresponding Japanese Patent Application No. 2015-015298.

* cited by examiner

LINK ASSEMBLY, FRAME, AND WALKING ASSISTANCE ROBOT

CROSS-REFERENCE TO RELATED APPLICATION

This application claims the benefit of Korean Patent Application No. P2014-37080, filed on Mar. 28, 2014 in the Korean Intellectual Property Office, the entire disclosure of which is incorporated herein by reference.

BACKGROUND

1. Field

Example embodiments relate to a link assembly and a frame that are flexible such that the link assembly and frame are capable of supporting weight while being in close contact with the body and/or a walking assistance robot having the same.

2. Description of the Related Art

A walking assistance robot may be used as an assistance apparatus that assists with a weakened muscular strength and weight according to the field of usage or may be used as a strengthening apparatus that increases a user's muscular strength and supports a load of a heavy object. To assist the wearer with supporting a load, a conventional assistance apparatus may be rigid, and, therefore may not come into close contact with the wearer's body, or may be too flexible such that the assistance apparatus may buckle rather than assisting the user with supporting the load.

SUMMARY

Some example embodiments relate to a link assembly and a frame, whereby the frame is configured of a plurality of links pivotally connected to one another is capable of being flexibly bent, and/or a walking assistance robot having the same.

Additional aspects of the example embodiments will be set forth in part in the description which follows and, in part, will be obvious from the description, or may be learned by practice thereof.

Some example embodiments relate to a link assembly.

In some example embodiments, the link assembly includes a first link having a pivoting portion and a supporting portion; and a second link that is connected to the first link and extends, the second link including a first guide which is disposed to correspond to the pivoting portion of the first link and at which the pivoting portion is disposed so that the first link and the second link make a rotary motion with respect to each other and a linear motion with respect to each other and a second guide that is disposed to correspond to the supporting portion of the first link and limits rotation of the supporting portion so that the first link is supported by the second link.

The first guide may include a first guide wall that supports the pivoting portion in a configuration in which the first link and the second link are rotated with respect to each other.

The second guide may include a second guide wall that extends in a direction of the linear motion and supports the supporting portion when the first link is rotated.

The first guide may include, if the first link and the second link are aligned in the direction of the linear motion, a mounting portion on which the pivoting portion is disposed, and an extension portion that extends from the mounting portion to be tilted.

The extension portion may include a first extension portion that is disposed at one side of the mounting portion based on a straight line extending in the direction of the linear motion and a second extension portion that is disposed at the other side of the mounting portion based on the straight line extending in the direction of the linear motion.

The first extension portion and the second extension portion may be disposed to be symmetrical based on a straight line that passes the mounting portion and extends in the direction of the linear motion.

The first guide may be disposed in a form of a curve having a lowest point or a highest point.

The second guide may be disposed to be spaced apart from the first guide in the direction of the linear motion.

The second guide may extend in the direction of the linear motion and may guide the supporting portion to be moved in the direction of the linear motion.

The pivoting portion may include a first pin, and the supporting portion may include a second pin that is disposed to be spaced apart from the first pin in the direction of the linear motion.

A first coupling portion at which the first guide and the second guide are formed, may be disposed at the second link.

Two second coupling portions may be disposed at the first link so as to face each other at regular intervals, and the first coupling portion may be inserted into a space between the two second coupling portions.

The pivoting portion and the supporting portion may be disposed at the second coupling portion and may pass through the first coupling portion.

A plurality of first links and a plurality of second links may be disposed, and the plurality of first links and the plurality of second links may be alternately connected to one another.

In other example embodiments, the link assembly may include a first link that extends along a user's leg and includes a first pin and a second pin spaced apart from the first pin; and a second link which is connected to the first link and extends and in which a first slot into which the first pin is coupled and a second slot into which the second pin is coupled, are formed, wherein the first slot and the second slot may be confined by the first pin and the second pin, respectively, and may be moved so that the first link and the second link are rotated with respect to each other and make a linear motion with respect to each other.

The first slot and the second slot may be formed to have different shapes.

The first slot may be formed in a form of a curve, and the second slot may be formed in a form of a straight line.

The first slot may extend in a direction that proceeds across a straight line direction of the second slot.

The first slot may be formed in a form of a symmetric curve.

The first slot may be formed in a form of a curve having a lowest point or a highest point.

The first link and the second link may simultaneously make a rotary motion with respect to each other and a linear motion with respect to each other, and a height of an end of the first link and a height of an end of the second link may be the same before and after the first link makes the rotary motion and the linear motion.

Other example embodiments relate to a walking assistance robot mounted on a user's body and configured to assist with the user's walking.

In some example embodiments, the walking assistance robot may include a first frame mounted on the user's thigh;

a second frame mounted on the user's calf; and a knee joint that pivotally connects the first frame and the second frame, wherein at least one of the first frame and the second frame may be configured of a plurality of links connected to one another and may be disposed to be in close contact with the user's body, and the plurality of links may include: a first link including a first pin and a second pin that are spaced apart from each other along the user's leg; and a second link that is connected to the first link and includes a first slot in which the first pin is disposed so that the first link and the second link make a rotary motion with respect to each other and a linear motion with respect to each other, and a second slot in which the second pin is disposed and which interferes rotation of the second pin so that the first slot is supported.

The first slot may include, if the first link and the second link are aligned in a vertical direction, a mounting portion on which the first pin is disposed, and an extension portion that extends along the vertical direction from the mounting portion to be tilted.

The extension portion may be disposed on a left or right side of the mounting portion.

The second slot may extend in the vertical direction, and if the first pin is supported by an inner sidewall of the extension portion disposed on the right side of the mounting portion, the second pin may be supported by a left support wall of the second slot, and if the first pin is supported by an inner sidewall of the extension portion disposed on the left side of the mounting portion, the second pin may be supported by a right support wall of the second slot.

As the frame is flexibly bent according to a curve of the user's body, the first pin and the second pin may be moved within the first slot and the second slot so that an entire length of the frame changes and a height of a particular point of the frame from the ground does not change.

Other example embodiments relate to a frame that is pivotally mounted on a user's body according to a curve of the user's leg.

The frame may include a plurality of links connected to one another so that the plurality of links make a linear motion with respect to each other.

In some example embodiments, the link assembly may include a plurality of alternating links, each of the plurality of links including a first end having a projecting tongue and a second end having a corresponding grove, the tongues and groves each including traversing bores therethrough such that the traversing bores allow a limited amount of rotational and linear movement between the plurality of links while supporting a compressive force applied therebetween.

In some example embodiments, the traversing bores associated with a first one of the tongue and grove include slots, the slots including a curved slot and a straight slot located symmetrical about an inflection point of the curved slot.

In some example embodiments, the traversing bores associated with a second one of the tongue and grove include coupling holes therethrough that correspond to the slots such that corresponding ones of the slots and coupling holes are configured to receive pins therethrough.

In some example embodiments, the curved slot is configured to receive a first pin and the second slot is configured to receive a second pin, such that the limited amount of rotational motion between the plurality of links is determined by a shape of the curved slot and the limited amount of linear motion between the plurality of links is determined by a length of the straight slot.

BRIEF DESCRIPTION OF THE DRAWINGS

These and/or other aspects of the example embodiments will become apparent and more readily appreciated from the following description of the embodiments, taken in conjunction with the accompanying drawings of which.

DETAILED DESCRIPTION

Figure 1:
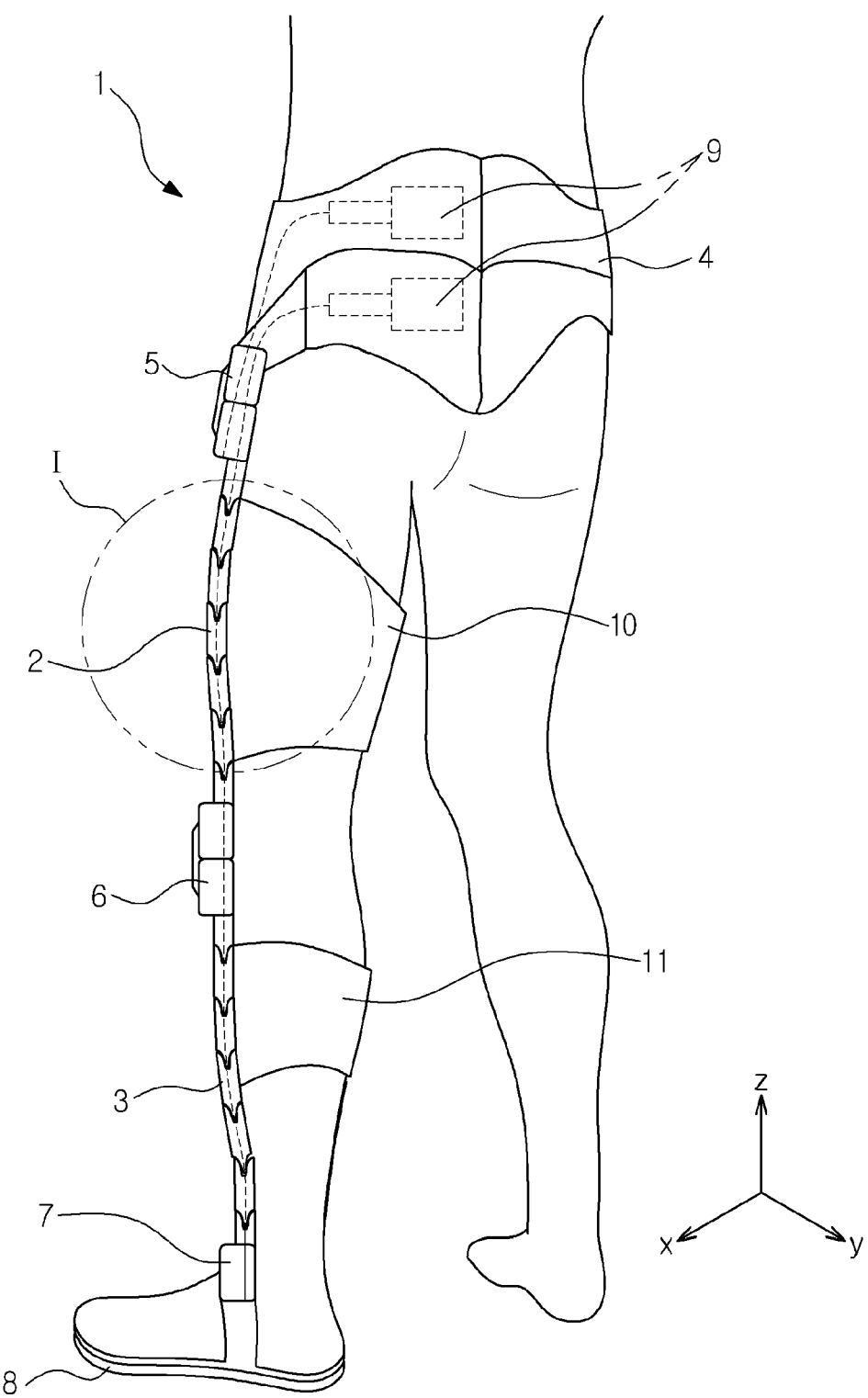
FIG. 1 is a conceptual view of a walking assistance robot having a buckle-free structure according to some example embodiments.

Reference will now be made in detail to example embodiments, some examples of which are illustrated in the accompanying drawings, wherein like reference numerals refer to like elements throughout.

It should be understood, however, that there is no intent to limit this disclosure to the particular example embodiments disclosed. On the contrary, example embodiments are to cover all modifications, equivalents, and alternatives falling within the scope of the example embodiments. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of this disclosure. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Various example embodiments will now be described more fully with reference to the accompanying drawings in which some example embodiments are shown. In the drawings, the thicknesses of layers and regions are exaggerated for clarity.

Figure 2:
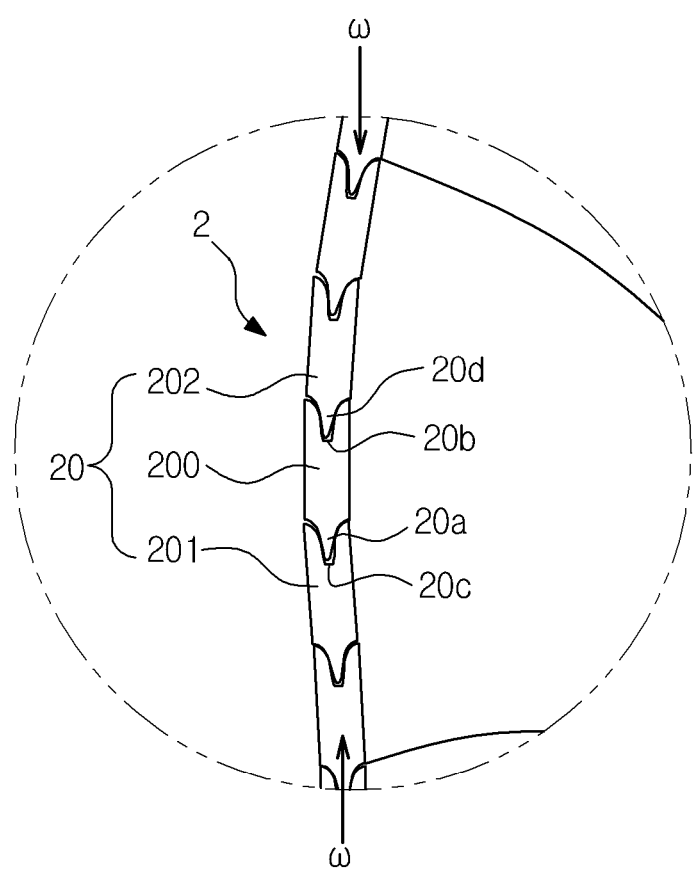
FIG. 2 is an enlarged view of portion I of FIG. 1.

FIG. 1 is a conceptual view of a walking assistance robot having a buckle-free structure according to some example embodiments, and FIG. 2 is an enlarged view of portion I of FIG. 1.

Referring to FIGS. 1 and 2, a walking assistance robot 1 includes frames 2 and 3 that extend along a lengthwise direction of a user's leg. The frames 2 and 3 may include a first frame 2 that supports the user's thigh and a second frame 3 that supports the user's calf.

The walking assistance robot 1 may further include a waist fixing unit 4 fixed to the user's waist and a foot structure 8 mounted on the user's foot. The first frame 2 and the waist fixing unit 4 may be connected to each other using a hip joint 5, and the first frame 2 and the second frame 3 may be connected to each other using a knee joint 6. Similarly, the second frame 3 and the foot structure 8 may be connected to each other using an ankle joint 7. The hip joint 5 causes the first frame 2 fixed to the user's thigh to be pivotally connected to the waist fixing unit 4, and the knee joint 6 causes the second frame 3 fixed to the user's calf to be pivotally connected to the first frame 2, and the ankle joint 7 causes the foot structure 8 to be pivotally connected to the second frame 3. The walking assistance robot 1 may further include a driving source 9 that provides a driving force to the hip joint 5 and the knee joint 6.

A first fixing unit 10 may be connected to the first frame 2 so as to fix the first frame 2 to the user's thigh. Similarly, a second fixing unit 11 may be connected to the second frame 3 so as to fix the second frame 3 to the user's calf. The first fixing unit 10 and the second fixing unit 11 may be provided in the form of a fastener.

The first fixing unit 10 and the second fixing unit 11 that fix the first and second frames 2 and 3 to be in close contact with the user's leg may be adjusted to be suitable for the user's leg size.

The waist fixing unit 4 may be formed of a flexible strap so as to be adjusted to be suitable for the user's waist size. For example, the waist fixing unit 4 may be a hook-end-loop fixing unit formed of Velcro or a strap including a fixing portion, such as a buckle, a ratchet buckle, or catch.

The hip joint 5 may be provided to have 3 degrees of freedom (DOF) so that the first frame 2 connected to the hip joint 5 may be pivoted around an x-axis, a y-axis, and a z-axis. The first frame 2 may be pivoted around the x-axis using the hip joint 5 to which the driving force is transferred from the driving source 9. The first frame 2 may also be pivoted around the y-axis using a hinge unit. The first frame 2 or the hip joint 5 to which the first frame 2 is connected, may be provided to be slidable along the waist fixing unit 4 so that the first frame 2 or the hip joint 5 may be pivoted around the z-axis. For example, a rail portion provided in an extension direction of the x-axis may be provided at the waist fixing unit 4, and a sliding portion may be provided at the first frame 2 or the hip joint 5 so that the sliding portion may slide along the rail portion according to the user's motion and the first frame 2 may be pivoted around the z-axis. In this way, by using the hip joint 5 having 3 degrees of freedom (DOF), the first frame 2 may be pivoted around the x-axis, the y-axis, and the z-axis so that the user's walking motion can be smoothly made.

The knee joint 6 may be provided to have 1 degree of freedom (DOF). For example, the knee joint 6 may pivot the first frame 2 or the second frame 3 around the x-axis using the driving force transferred from the driving source 9.

A DOF may mean the number of independent motions of a mechanism, or the number of independent parameters that are required to specify an independent motion at a relative position with respect to links.

The ankle joint 7 may be provided to have 3 degrees of freedom, like the hip joint 5. For example, the second frame 3 or the foot structure 8 may be provided around the x-axis, the y-axis, and the z-axis based on the ankle joint 7.

The foot structure 8 may be mounted on the user's foot. A sensor may be provided on a bottom surface of the foot structure 8 on which the user's foot contacts, may detect a change in a load of the user who wears the walking assistance robot 1, and may transmit information regarding the detected change in the user's load to a controller (not shown). The controller (not shown) may control a motion of the hip joint 5 or the knee joint 6 using the information detected by the sensor.

The controller may include a processor and a memory (not shown).

The controller may include a processor, for example, a central processing unit (CPU), a controller, or an application-specific integrated circuit (ASIC), that when, executing instructions stored in the memory, configures the controller as a special purpose machine to move the first and second frames 2 and 3 with a desired amount of force.

The first frame 2 and/or the second frame 3 may be configured of a plurality of links 20 connected to one another. A wedge may be formed to protrude from one side of each of the plurality of links 20, and a wedge groove may be formed in the other side of each link 20 so as to correspond to a shape of the wedge. For example, a wedge formed on a first link 200 of the plurality of links 20 associated with the first frame 2 may be inserted into a wedge groove formed in a second link 201 of the plurality of links 20 associated with the first frame 2. Further, a wedge formed on a third link 202 associated with the first frame 2 may be inserted into a wedge groove formed in the first link 200. Therefore, the plurality of links 20 may be connected to one another. The first link 200, the second link 201 and the third link 202 may be provided to have the same or similar shape. More particularly, a wedge 20a may be formed at one side of the first link 200, and the wedge 20*a* may be inserted into a wedge groove 20*c* of the second link 201. A wedge groove 20*b* may be formed at the other side of the first link 200, and a wedge 20*d* formed at the third link 202 may be inserted into the wedge groove 20*b*.

In the second frame 3, like in the first frame 2, a wedge may be formed at one side of each of a plurality of links, and a wedge groove may be formed in the other side of each link. Also, the plurality of links may be connected to one another in such a way that a wedge of another link is inserted into a wedge groove of one link that constitutes the second frame 3.

Hereinafter, the user's load supported by the plurality of links 20 that constitutes the first frame 2 will be described. The following discussion of the first frame 2 may be similarly applied to the second frame 3.

The first frame 2 or the second frame 3 is configured of the plurality of links 20 connected to one another, as described above, so that, when the user wears the walking assistance robot 1, the walking assistance robot 1 corresponds to a shape of the user's body that contacts the walking assistance robot 1 and thus the first frame 2 or the second frame 3 can be flexibly bent. Thus, the frame may maintain close contact with the user's body so that a sense of wearing of the walking assistance robot 1 may be improved. Further, because the frame may maintain close contact with the user's body, a size of the walking assistance robot 1 may be reduced.

If the user wears the walking assistance robot 1, a compressive force w may be transferred to the first frame 2 configured of the plurality of links 20 connected to one another, in a lengthwise direction of the first frame 2 by the user's load. The compressive force w may be transferred to the plurality of links 20 that constitute the first frame 2, and the wedge 20*a* formed at the first link 200 may be inserted into the wedge groove 20*c* formed in the second link 201 adjacent to the first link 200 and may be supported by an inner sidewall of the wedge groove 20*c*. The wedge 20*a* is supported by the inner sidewall of the wedge groove 20*c* so that the first link 200 may be supported by the second link 201. In this way, the user's load may be supported by the first frame 2 using a configuration in which one link is supported by another link disposed in a lower position.

Hereinafter, for the sake of brevity a single first frame 2 and second frame 3 will be described, but the corresponding descriptions may be equally applied to pairs of the respective structure units, for example, left and right versions thereof.

Figure 3:
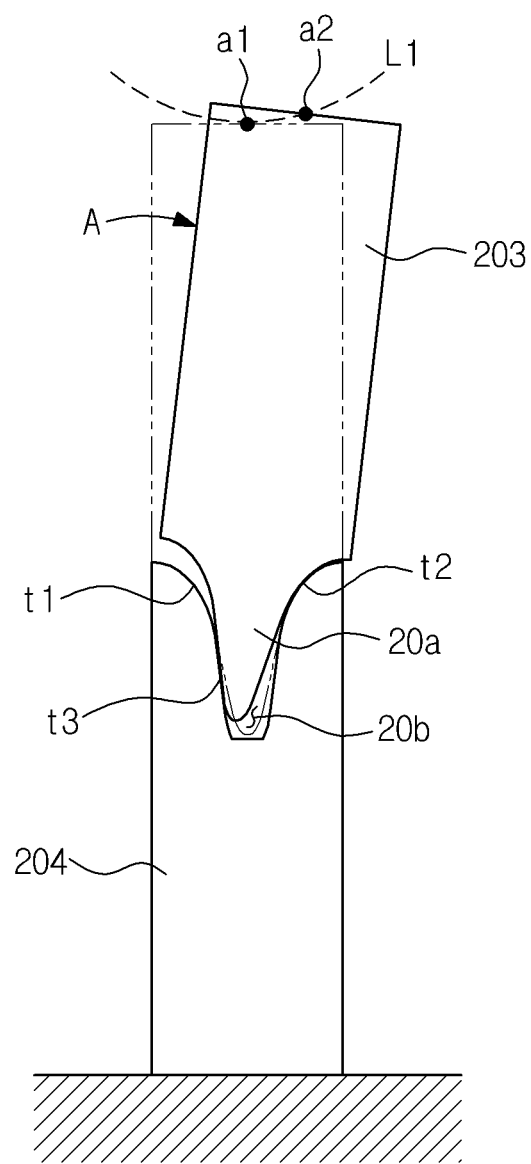
FIG. 3 is a view for describing a link structure of the walking assistance robot illustrated in FIG. 1.
Figure 4:
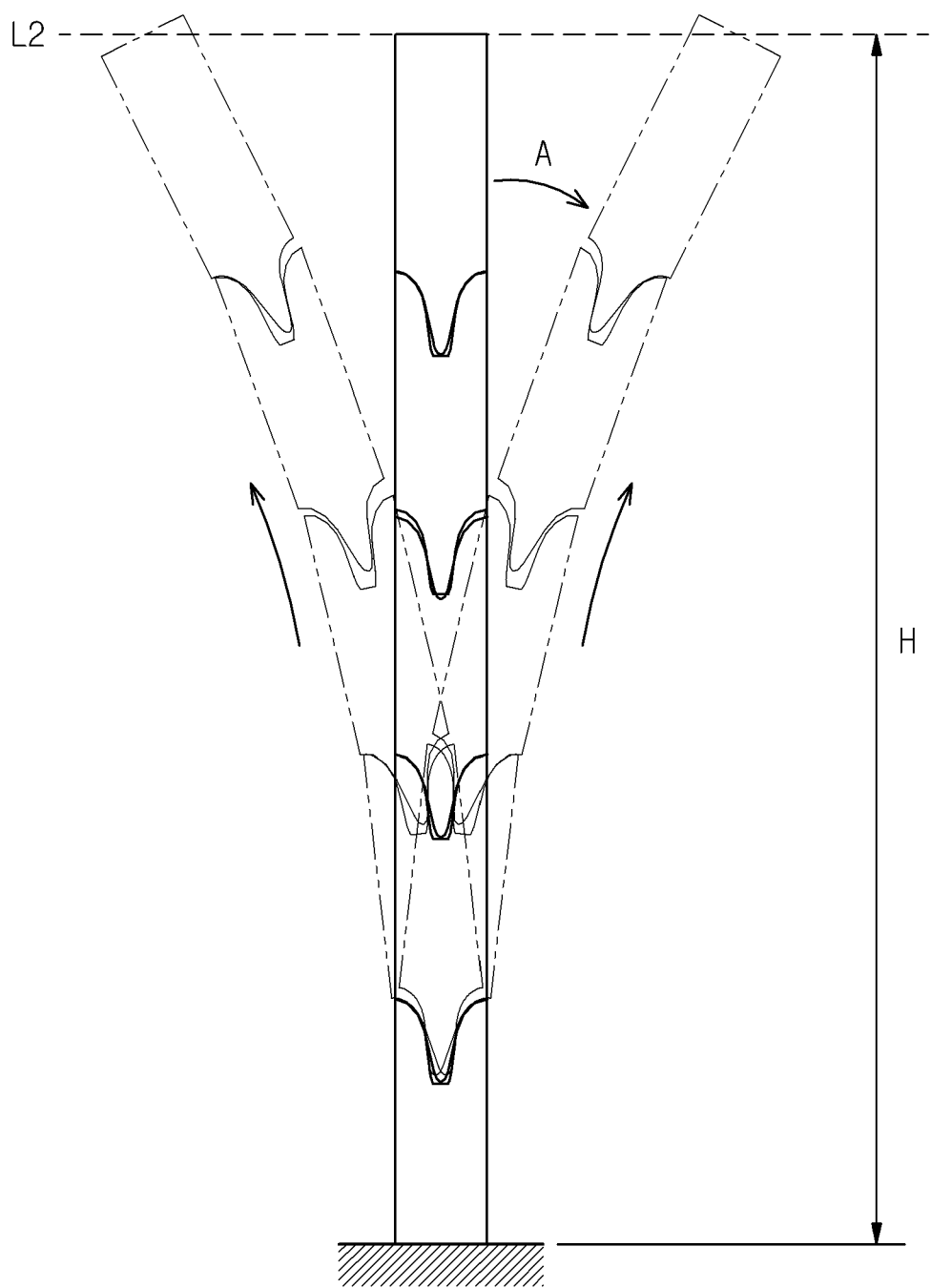
FIG. 4 is a conceptual view of a multi-link structure of the walking assistance robot of FIG. 1.

FIG. 3 is a view for describing a link structure of the walking assistance robot illustrated in FIG. 1, and FIG. 4 is a conceptual view of a multi-link structure of the walking assistance robot of FIG. 1.

As illustrated in FIG. 3, the plurality of links 20 may include an upper link 203 and a lower link 204. The upper link 203 may be supported by the lower link 204. The wedge 20*a* formed on the upper link 203 may be inserted into the wedge groove 20*b* formed in the lower link 204 so that the upper link 203 and the lower link 204 may be connected to each other. If the upper link 203 forms a straight line with the lower link 204 perpendicularly to a ground, the wedge 20*a* of the upper link 203 may be completely inserted into the wedge groove 20*b* of the lower link 204 so that a bottom surface of the upper link 203 or one surface of the wedge 20*a* contacts top surfaces t1 and t2 of the lower link 204. As a result, the upper link 203 is supported by t1 and t2 that are contact surfaces between the upper link 203 and the lower link 204.

If the upper link 203 is rotated in a direction A, the wedge 20*a* slides along the inner sidewall of the wedge groove 20*b* in an upward direction. An inner surface t3 of the wedge groove 20*b* contacts the wedge 20*a* and serves as a guide that guides motion. If the upper link 203 is rotated in the direction A and then an external force is removed from the upper link 203, the upper link 203 may be supported not to be further rotated by t2 and t3 of the lower link 204 and may withstand the compressive force applied to a link assembly.

For example, the contact surface t2 may support a vertical load applied to the link assembly, and the contact surface t3 may resist further rotation of the upper link 203. A distance between a lowest point of the wedge 20*a* and a lowest point of the wedge groove 20*b* may be increased after the upper link 203 is rotated, compared to before rotation.

Since it may be regarded that the upper link 203 is pivoted around t2, the contact surface t2 on which the upper link 203 and the lower link 204 contact each other, may be referred to as a pivoting portion. Also, since the wedge 20*a* of the upper link 203 is supported by t3 that is the inner sidewall of the wedge groove 20*b* of the lower link 204 and rotation of the upper link 203 is limited, t3 may be referred to as a supporting portion or a rotation limitation portion.

An inner surface of the wedge groove 20*b* disposed at t3 may be referred to as a first guide that guides motion of the wedge 20*a*. When the upper link 203 is rotated in an opposite direction to the direction A of FIG. 3, an inner surface of the lower link 204 disposed at t2 guides a motion of the wedge 20*a* and thus may be referred to as a second guide.

As the upper link 203 is rotated, a top end of the upper link 203 may be moved in the direction A by drawing a downwardly-concave curve L1. The top end of the upper link 203 before rotation may be disposed at a1 that is a lowest point of the curve L1. After rotation, the upper link 203 may ascend toward a2 on the curve L1. As the upper link 203 is rotated, the shape of the curve L1 drawn by the top end of the upper link 203 may vary according to shapes of the wedge 20*a* and the wedge groove 20*b*. For example, unlike in FIG. 3, a slope of the curve L1 drawn by the top end of the upper link 203 may be set to 0. In detail, by implementing the wedge 20*a* and the wedge groove 20*b* in an appropriate form, when the upper link 203 is rotated, the top end of the upper link 203 may be moved along a straight line that is horizontal with respect to the ground.

By designing the wedges 20*a* and the wedge grooves 20*b* included in the plurality of links 20 associated with the first frame 2 in such form, even when the first frame 2 is bent, the height of the first frame 2 may not change from a particular point. For example, by properly adjusting curvatures of the wedge 20*a* and the wedge groove 20*b*, even when the first frame 2 is bent, as illustrated in FIG. 4, the particular point of the first frame 2 from the ground may be placed in the same straight line L2 that is parallel to the ground. Through this configuration, a height H of the first frame 2 may be maintained to be the same before and after the first frame 2 is bent.

Therefore, even when a curve of the body varies according to the user's walking motion, the first frame 2 may bend according to a change in the curve of the body so that the user's sense of wearing can be improved. The first frame 2 is formed to have a buckle-free structure in which, even when the first frame 2 is bent, buckling does not occur, and thus, the first frame 2 can support the load in the vertical direction. Also, even when the first frame 2 is bent, the particular point of the first frame 2 from the ground may be placed in a straight line parallel to the ground so that the height of the first frame 2 is not decreased according to the change in the curve of the body and thus the user can walk comfortably.

Hereinafter, an example embodiment of a walking assistance robot using the buckle-free structure will be described.

Figure 5:
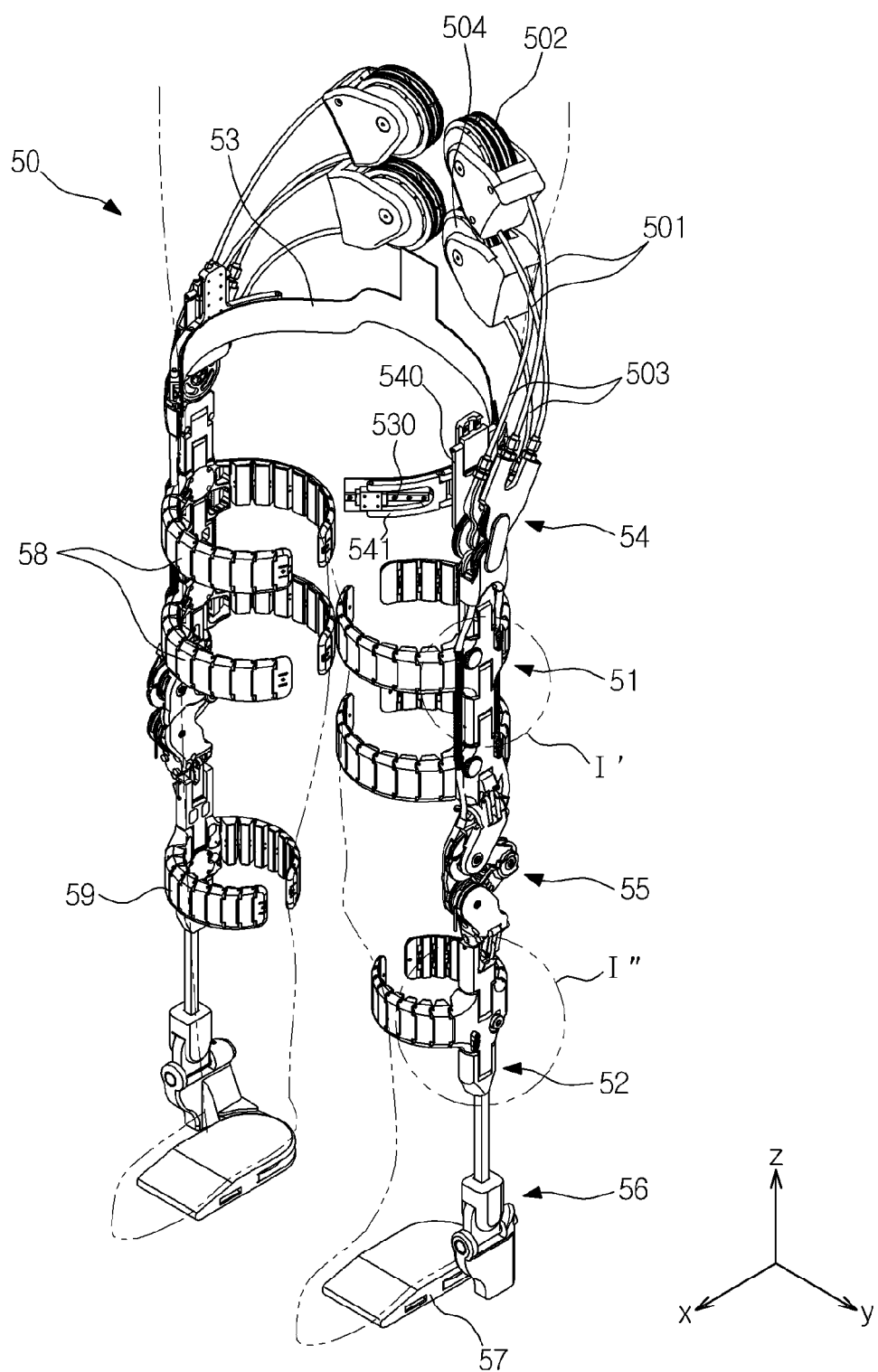
FIG. 5 is a view for describing a walking assistance robot according to some example embodiments.

FIG. 5 is a view for describing a walking assistance robot according to other example embodiment.

Referring to FIG. 5, a walking assistance robot 50 may include frames 51 and 52 that extend in the lengthwise direction of the user's leg and support the user's load. The frames 51 and 52 may include a first frame 51 that supports the user's thigh and a second frame 52 that supports the user's calf.

A waist fixing unit 53 fixed to the user's waist may be connected to the first frame 51. The first frame 51 may be pivotally connected to the waist fixing unit 53 using a hip joint 54. The first frame 51 and the second frame 52 may be pivotally connected to each other using a knee joint 55. A foot structure 57 fixed to the user's foot may be connected to the second frame 52. The second frame 52 and the foot structure 57 may be pivotally connected to each other using an ankle joint 56.

The walking assistance robot 50 may further include a driving source that provides a driving force to the hip joint 54 and the knee joint 55 and a controller that controls an operation of the walking assistance robot 50. A sensor may be provided at the foot structure 57, and information regarding the user's motion detected by the sensor may be transmitted to the controller, and the controller may control the motion of the hip joint 54 or the knee joint 55 using the transmitted information.

The first frame 51 may be pivoted to have 3 degrees of freedom. The first frame 51 may be pivoted around the y-axis by reducing or extending a wire 501. The wire 501 may be wound around a pulley 502 connected to the driving source and may be connected to the first frame 51 using the hip joint 54. For example, when the driving source rotates the pulley 502 and causes the wire 501 to be wound around the pulley 502, the first frame 51 may be pivoted around the y-axis. If the driving source rotates the pulley 502 and causes the wire 501 to be unwound from the pulley 502, the first frame 51 may be pivoted around the y-axis in an opposite direction to a direction of the previous case.

The hip joint 54 may be rotated around the x-axis using a hinge unit 540. If the hip joint 54 is rotated by the hinge unit 540, the first frame 51 connected to the hip joint 54 may be pivoted around the x-axis.

A sliding portion 541 may be disposed on a rear surface of the hinge unit 540, and a rail portion 530 may be disposed at the waist fixing unit 53. The rail portion 530 may extend in a direction of the x-axis that is a direction of the user's waist. The sliding portion 541 may slide along the rail portion 530 according to the user's motion. The sliding portion 541 slides along the rail portion 530 so that the hip joint 54 and the first frame 51 that are connected to the hinge unit 540 may be pivoted around the z-axis.

In this way, the first frame 51 may be pivoted to have 3 degrees of freedom using the hip joint 54, the hinge unit 540, and the rail portion 530.

An operation with 1 degree of freedom pivoted around the hip joint 54 using the wire 501 may be performed by power, however, an operation of the other 2 degrees of freedom may be performed according to the user's motion without using power.

The second frame 52 may be pivoted to have 1 degree of freedom with respect to the first frame 51. The second frame 52 that is pivotally connected to the first frame 51 by the knee joint 55 may be pivoted by reducing or extending a wire 503. The wire 503 may be wounded around a pulley 504 connected to the driving source and may be connected to the second frame 52 by the knee joint 55. For example, if the driving source rotates the pulley 504 and causes the wire 503 to be wound around the pulley 504, the second frame 52 may be pivoted around the y-axis. If the driving source rotates the pulley 504 and the wire 503 is unwound from the pulley 504, the second frame 52 may be pivoted around the y-axis in an opposite direction to a direction of the previous case.

The foot structure 57 may be pivoted to have 3 degrees of freedom with respect to the second frame 52. The foot structure 57 and the second frame 52 may be pivotally connected to each other by the ankle joint 56. The foot structure 57 or the second frame 52 may be pivoted around the ankle joint 56 according to the user's motion without using power.

A first fixing unit 58 may be connected to the first frame 51. The first fixing unit 58 may surround the user's thigh and may cause the first frame 51 to be mounted on the user's thigh. A second fixing unit 59 may be connected to the second frame 52. The second fixing unit 59 may surround the user's calf and may cause the second frame 52 to be mounted on the user's calf.

If the user wears the walking assistance robot 1, the first frame 51 or the second frame 52 may be provided to extend in the lengthwise direction of the user's leg. The first frame 51 and/or the second frame 52 are configured of a plurality of links that are formed of a rigid material and are pivotally connected to one another, so that the first frame 51 and/or the second frame 52 may be flexibly bent according to a curve of the user's body and may support the user's load stably.

Hereinafter, a structure of the first frame 51 will be described. The following contents of the first frame 51 may be similarly applied to the second frame 52.

Figure 6:
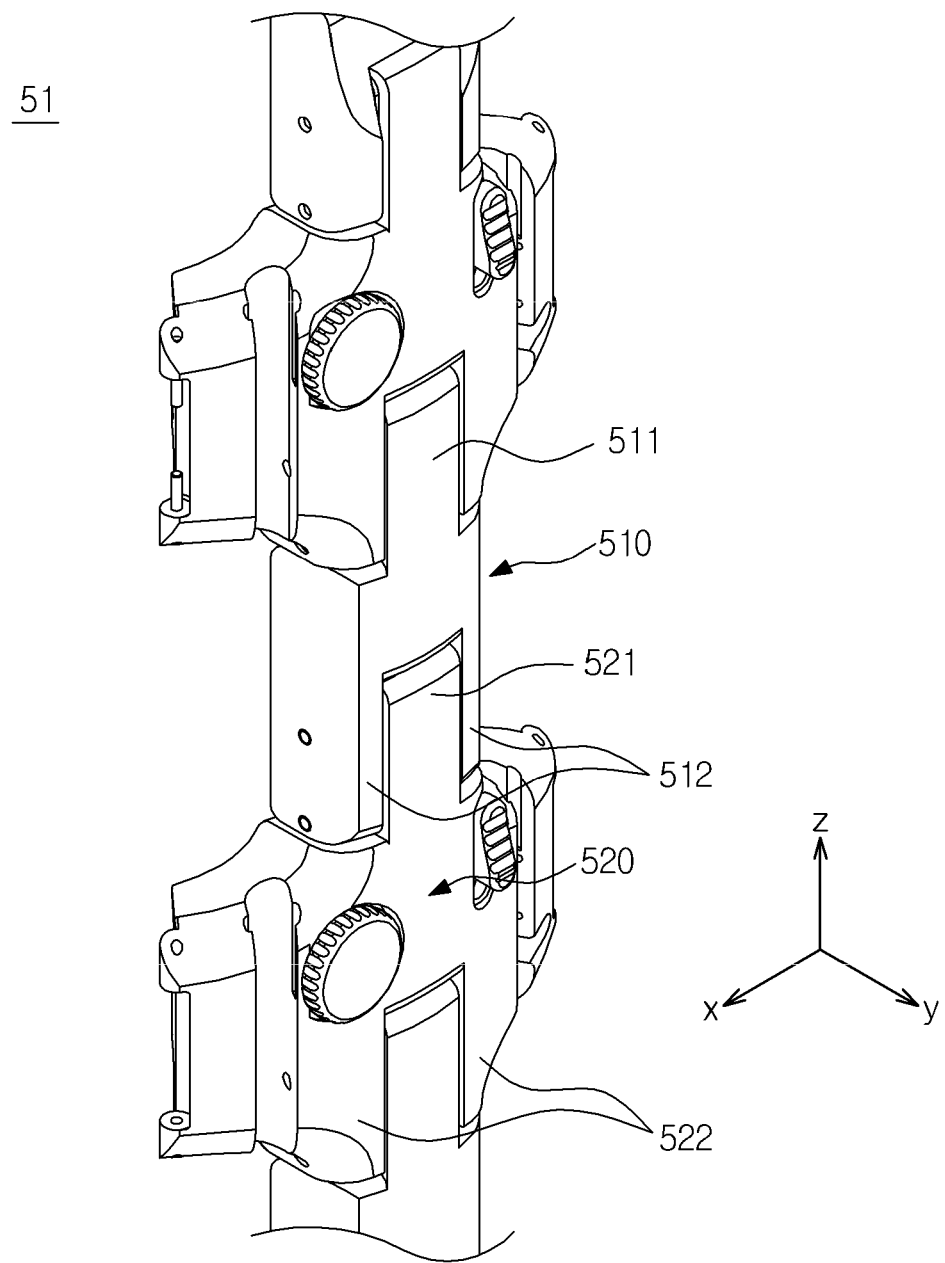
FIG. 6 is an enlarged view of portion I' of FIG. 5.
Figure 7:
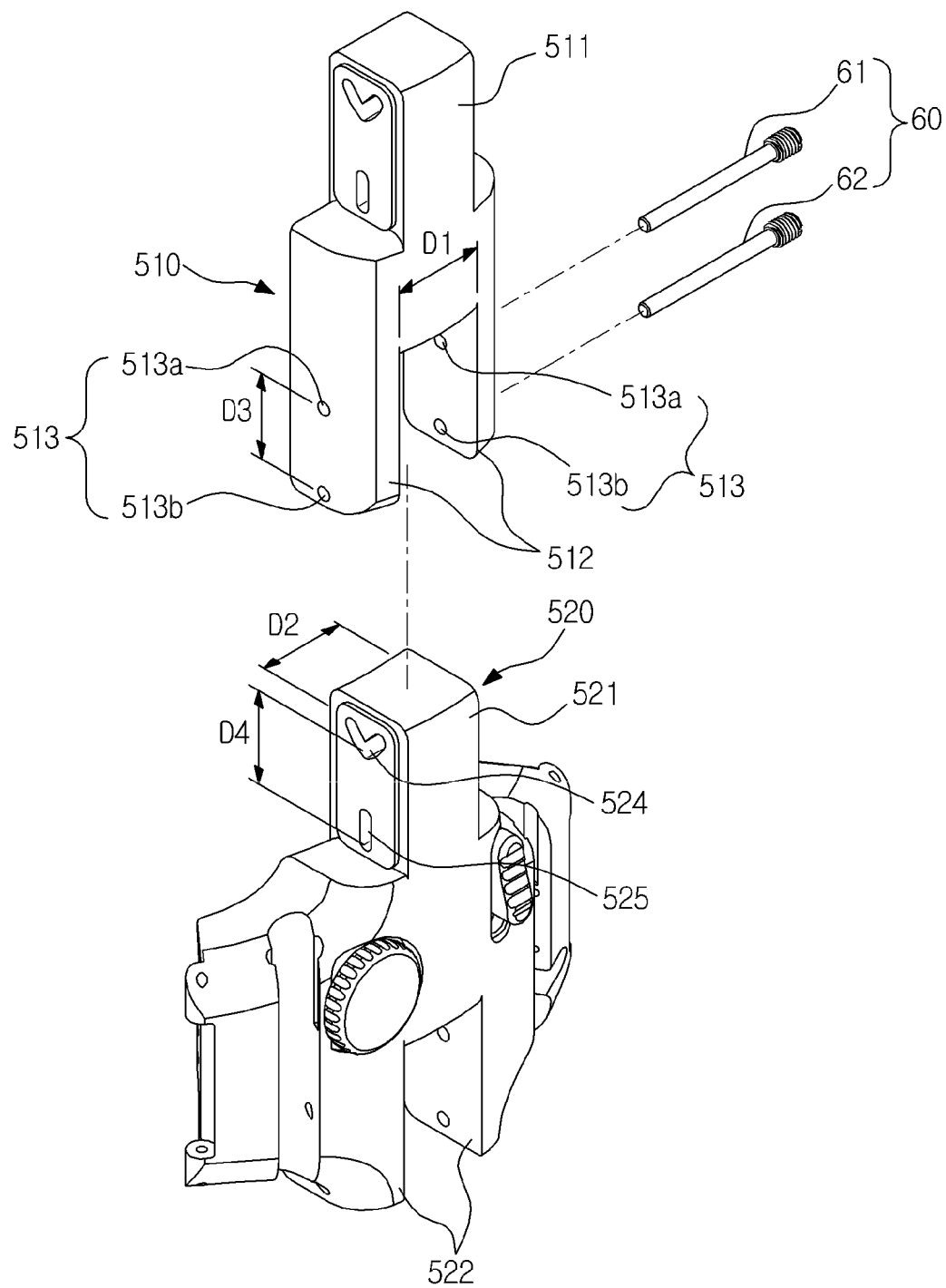
FIG. 7 is an exploded perspective view of FIG. 6.
Figure 8:
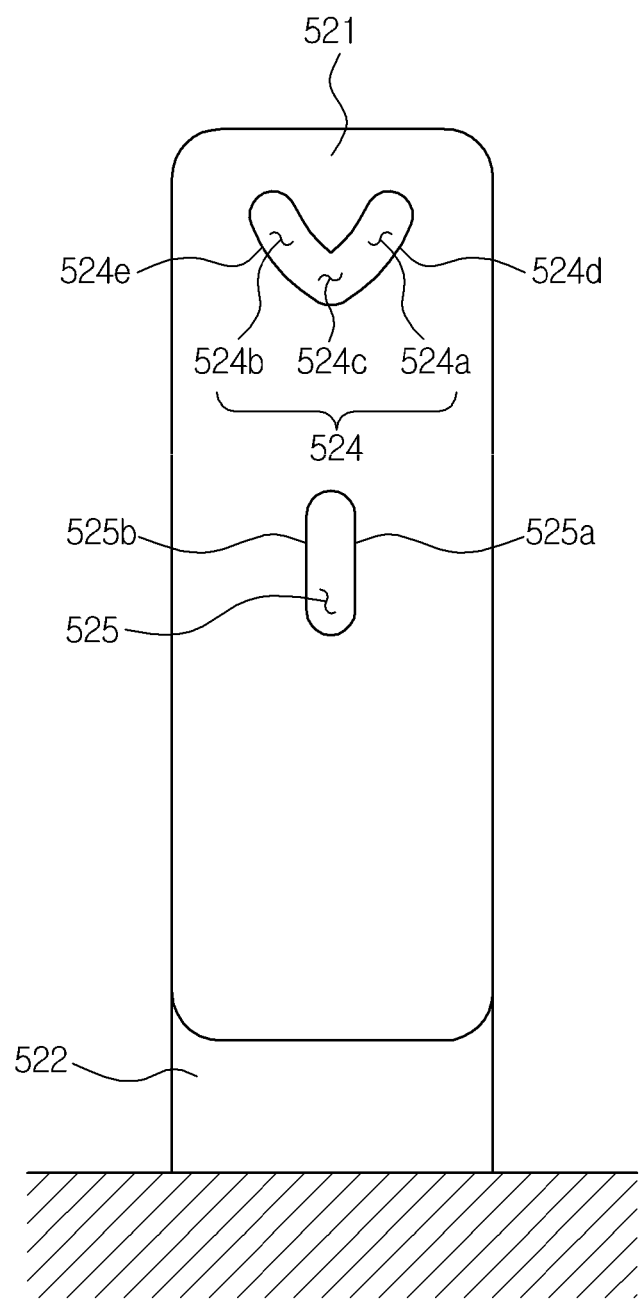
FIG. 8 is a view of a first coupling portion of a link illustrated in FIG. 7.

FIG. 6 is an enlarged view of portion I' of FIG. 5, and FIG. 7 is an exploded perspective view of FIG. 6, and FIG. 8 is a view of a first coupling portion of a link illustrated in FIG. 7.

Referring to FIGS. 6 through 8, the first and second frames 51 and 52 of the walking assistance robot 50 may be configured of the plurality of links connected to one another. Hereinafter, for the sake of brevity, an example embodiment in which the first frame 51 is configured of a plurality of links connected to one another, will be described. However, example embodiments equally apply to the second frame The first frame 51 may be configured of a plurality of links and thus may be flexibly bent according to a curve of the thigh on which the first frame 51 is mounted, and the first frame 51 may support the user's load stably.

The plurality of links that constitute the first frame 51 may be connected to one another to be pivoted around the x-axis. One of the plurality of links that constitute the first frame 51 may be referred to as a first link 510, and another link connected to the first link 510 may be referred to as a second link 520. The first link 510 and the second link 520 may be connected to each other so as to be pivoted around the x-axis, and this connection structure may be referred to as a link assembly. The first frame 51 may be configured of a plurality of first links 510 and a plurality of second links 520 that are alternately disposed. The plurality of first links 510 and the plurality of second links 520 that constitute the first frame 51 are pivotally connected to one another so that the plurality of first links 510 and the plurality of second links 520 may be pivoted at an appropriate angle according to the curve of the thigh that the first frame 51 contacts. Thus, the first frame 51 may be in close contact with the thigh.

The first link 510 may include a first coupling portion 511 and a second coupling portion 512. The first coupling portion 511 may be formed to protrude from one side of the first link 510. The second coupling portion 512 may be formed to protrude from the other side that faces the one side at which the first coupling portion 511 is formed. Two second coupling portions 512 that face each other may be formed to protrude.

The second link 520 may also include a first coupling portion 521. The first coupling portion 51 formed at the second link 520 adjacent to the first link 510 may be inserted into a space between the two second coupling portions 512 of the first link 510. The space between the second coupling portions 512 may be referred to as a first coupling portion accommodation portion. A distance between the second coupling portions 512 may be equal to or a little greater than a width D2 of the first coupling portion 521 formed at the adjacent second link 520.

The first link 510 and the second link 520 may be connected to each other by a pivoting portion and a supporting portion and may make a rotary motion and a linear motion in an extension direction of the link assembly. If the extension direction of the link assembly is referred to as a first direction, the first link 510 may simultaneously make a rotary motion with respect to the second link 520 and a linear motion in the first direction. When the link assembly extends in the vertical direction, the first direction may be an upward direction of the link assembly.

The first link 510 and the second link 520 may be connected to each other by pins 60. When the first link 510 is rotated, the first link 510 may make a linear motion in the first direction that proceeds across a rotation direction. In this case, the pins 60 may be guided by guides formed at the second link 520. The pins 60 may include a first pin 61 and a second pin 62.

A first guide that guides the first pin 61 and a second guide that guides the second pin 62 may be disposed at the second link 520. The first guide and the second guide may have the form of slots into which the first pin 61 and/or the second pin 62 may be inserted. In FIGS. 7 and 8, the first guide into which the first pin 61 is inserted, is a first slot 524, and the second guide into which the second pin 62 is inserted, is a second slot 525.

When the first pin 61 is guided by the first guide and the first link 510 is rotated with respect to the second link 520, the first link 510 may be linearly moved in the first direction with respect to the second link 520.

As illustrated in FIG. 8, the first slot 524 includes a mounting portion 524*c* on which the first pin 61 is mounted, when the first link 510 and the second link 520 are aligned in a straight line in the first direction. The first slot 524 includes extension portions 524*a* and 524*b* that extend from the mounting portion 524*c* based on the straight line that extends in the first direction. The extension portions 524*a* and 524*b* may extend from the left or right side of the mounting portion 524*c* to be tilted in the first direction. For example, the extension portions 524*a* and 524*b* may be formed in the form of curves that are symmetrical based on the mounting portion 524*c* so that they are oriented to a left upward direction or a right upward direction from the mounting portion 524*c*.

A first guide wall 524*d* that is an inner sidewall of the first extension portion 524*a* and a second guide wall 524*e* that is an inner sidewall of the second extension portion 524*b* may support the first pin 61. The first pin 61 is moved along the first slot 524 so that the first link 510 may be rotated with respect to the second link 520. Thus, a structure including the first pin 61 or the first pin 61 and the first slot 524 may be referred to as a pivoting portion.

The second slot 525 may be spaced apart from the first slot 524 in the first direction and may be disposed above or below the first slot 524. The second slot 525 may be formed in the form of a straight line that extends in the first direction. A right inner surface that constitutes the second slot 525 may be referred to as a first support wall 525*a*, and a left inner surface that constitutes the second slot 525 may be referred to as a second support wall 525*b*. The second pin 62 may be supported by a support wall and may limit rotation of the first link 510. Thus, a structure including the second pin 62 or the second pin 62 and the second slot 525 may be referred to as a supporting portion or a rotation limitation portion.

When the first pin 61 is supported by the first guide wall 524*d* that constitutes the first extension portion 524*a* disposed on the right of the first slot 524, the second pin 62 may be supported by the second support wall 525*b* disposed on the left of the second slot 525. Contrary to this, when the first pin 61 is supported by the second guide wall 524*e* that constitutes the second extension portion 524*b* disposed on the left of the first slot 524, the second pin 62 may be supported by the first support wall 525*a* disposed on the right of the second slot 525. In other words, the first pin 61 and the second pin 62 may be supported by inner sidewalls of slots disposed in opposite directions.

As illustrated in FIG. 8, the first slot 524 may be formed in the form of a curve having a lowest point or a highest point. The first slot may be formed in the form of an asymmetric curve, instead of the form of a bilateral symmetry curve. By varying a degree of bending according to a rotation direction, the form of the asymmetric curve may be used as needed.

Hereinafter, an example embodiment in which the first slot 524 is formed in the form of a concave curve in a downward direction in which the mounting portion 524*c* is set to the lowest point and the second slot 525 is formed in the form of a straight line that extends in the vertical direction and the second slot 525 is disposed below the first slot 524, will be described. However, example embodiments are not limited thereto.

As illustrated in FIG. 7, coupling holes 513 into which the pins 60 may be inserted, may be formed in the second coupling portions 512 of the first link 510. Two coupling holes 513 may be formed in two second coupling portions 512 so as to be spaced apart from each other in the vertical direction. A distance D3 between the two coupling holes 513 may be equal to a distance D4 between the lowest point of the first slot 524 and the lowest point of the second slot 525 that are formed in the adjacent second link 520.

The second link 520 connected to the first link 510 may be disposed in a similar form to that of the first link 510. For example, the second link 520 may include the first coupling portion 521 and second coupling portions 522. The first coupling portion 521 may be formed to protrude from one side of the second link 520, and the second coupling portion 522 may be formed to protrude from the other side of the second link 520 that faces a position where the first coupling portion 521 is formed. Two second coupling portions 522 may be formed to protrude and to face each other so that the first coupling portion 521 formed at the second link 520 adjacent to the first link 510 may be inserted into a space between the two second coupling portions 522.

The first pin 61 may pass through a coupling hole 513a disposed at an upper portion, among the coupling holes 513 formed in the first link 510 and the first slot 524 formed in the second link 520. The second pin 62 may pass through a coupling hole 513b disposed at a lower portion, among the coupling holes 513 formed in the first link 510 and the second slot 525 formed in the second link 520. A head having a larger size than that of the coupling hole 513 may be disposed on one end of each of the pins 61 and 62 and may prevent the pins 61 and 62 from escaping from the pin coupling hole 513 and the first slot 524 and the second slot 525. Also, a fixing member (not shown) may be coupled to the other end of each of the pins 61 and 62 and may prevent the pins 61 and 62 from escaping from the pin coupling hole 513, the first slot 524, and the second slot 525.

If the first link 510 or the second link 520 is pivoted, the first pin 61 may be moved along the first slot 524, and the second pin 62 may be moved along the second slot 525. Hereinafter, an operation of the pins 61 and 62 according to pivoting of the link assembly to which the first link 510 and the second link 520 are connected, will be described.

The first coupling 511 and the second coupling 512 may have a shape of one of a projecting tongue and a corresponding grove and the coupling holes 513 and slots 524 and 525 may be traversing bores having the aforementioned shapes such that the tongues and groves are pivotably connected via the pins 60 inserted into the transverse bore provided through the tongue and groove of adjacent first and second couplings 511, 512.

Figure 9:
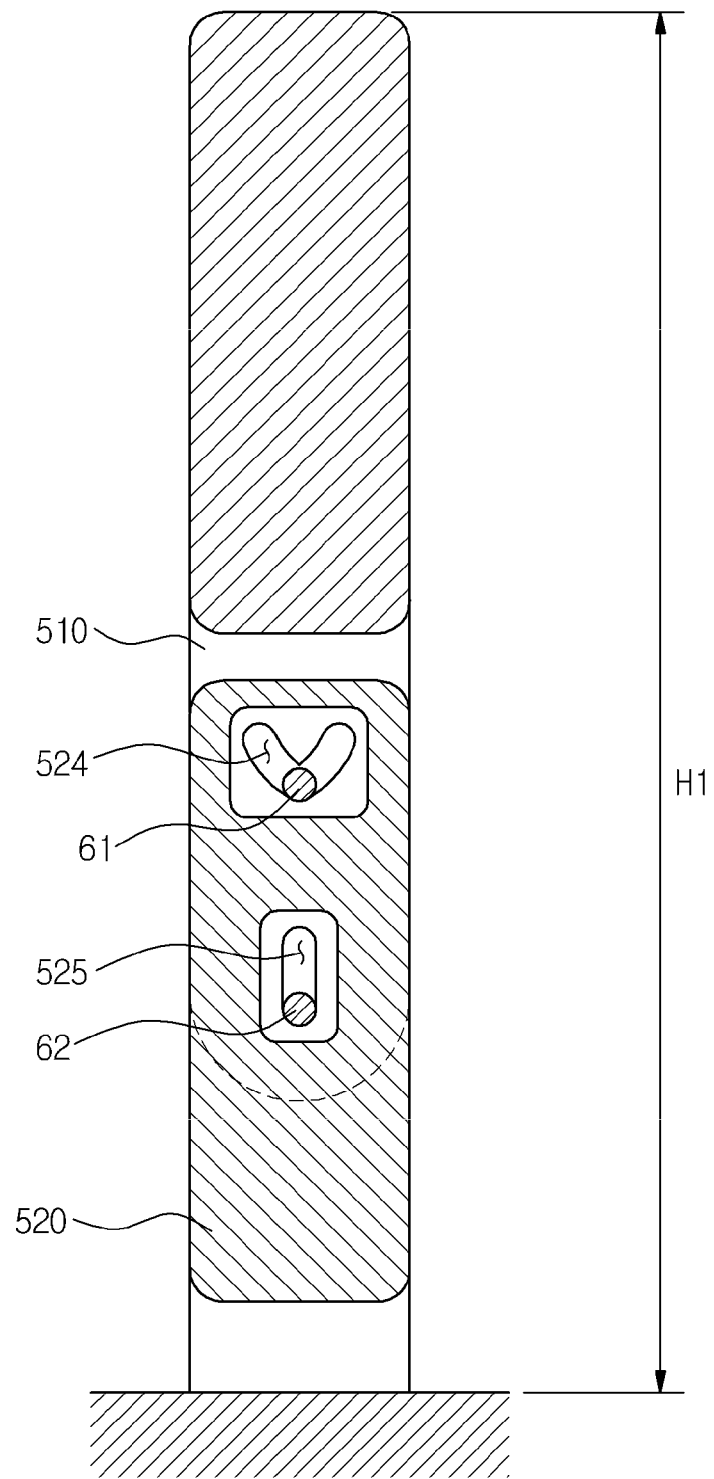
FIGS. 9 and 10 are views of positions of pins according to an operation of the link illustrated in FIG. 6.
Figure 10:
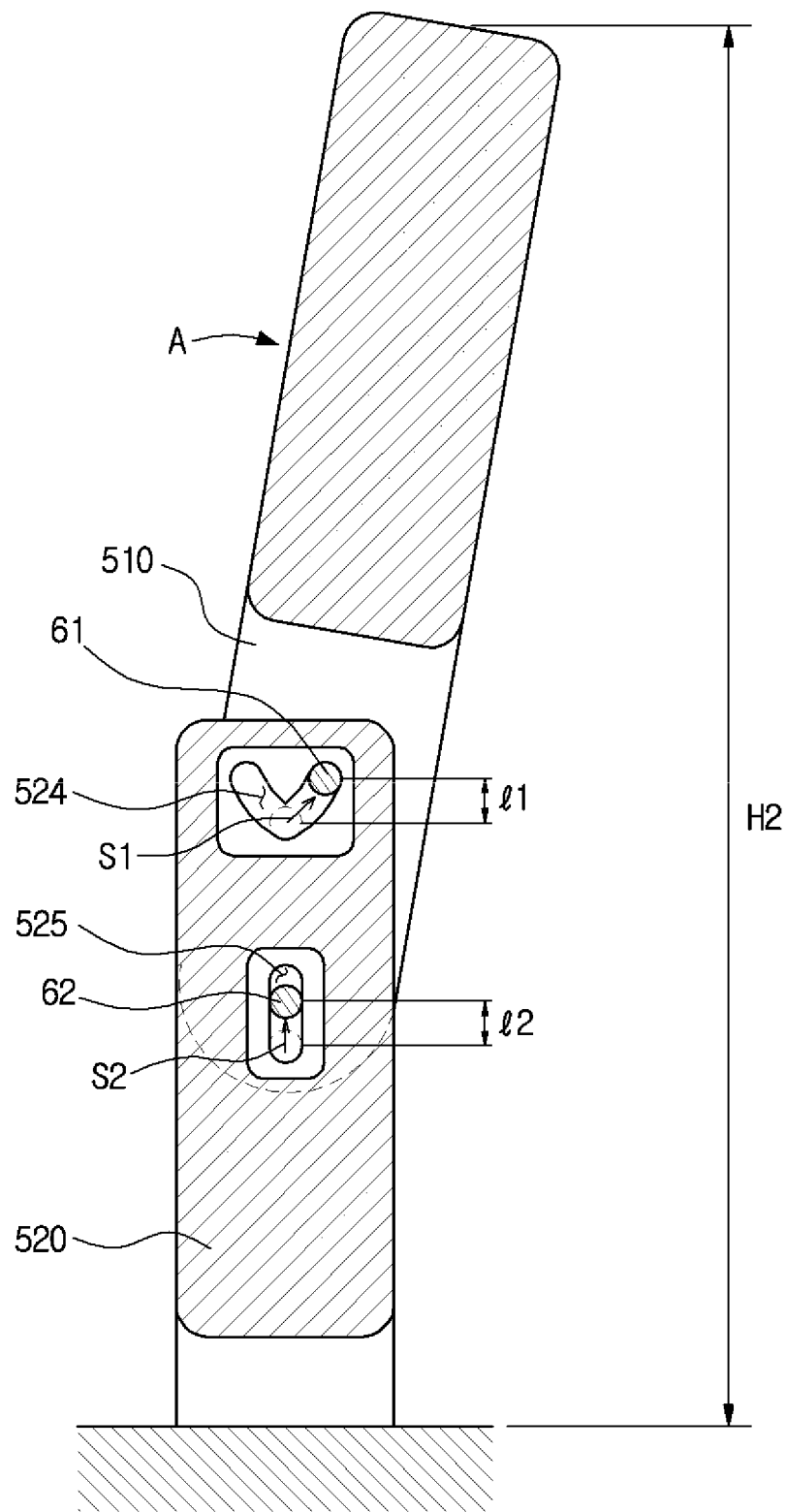
Figure 11:
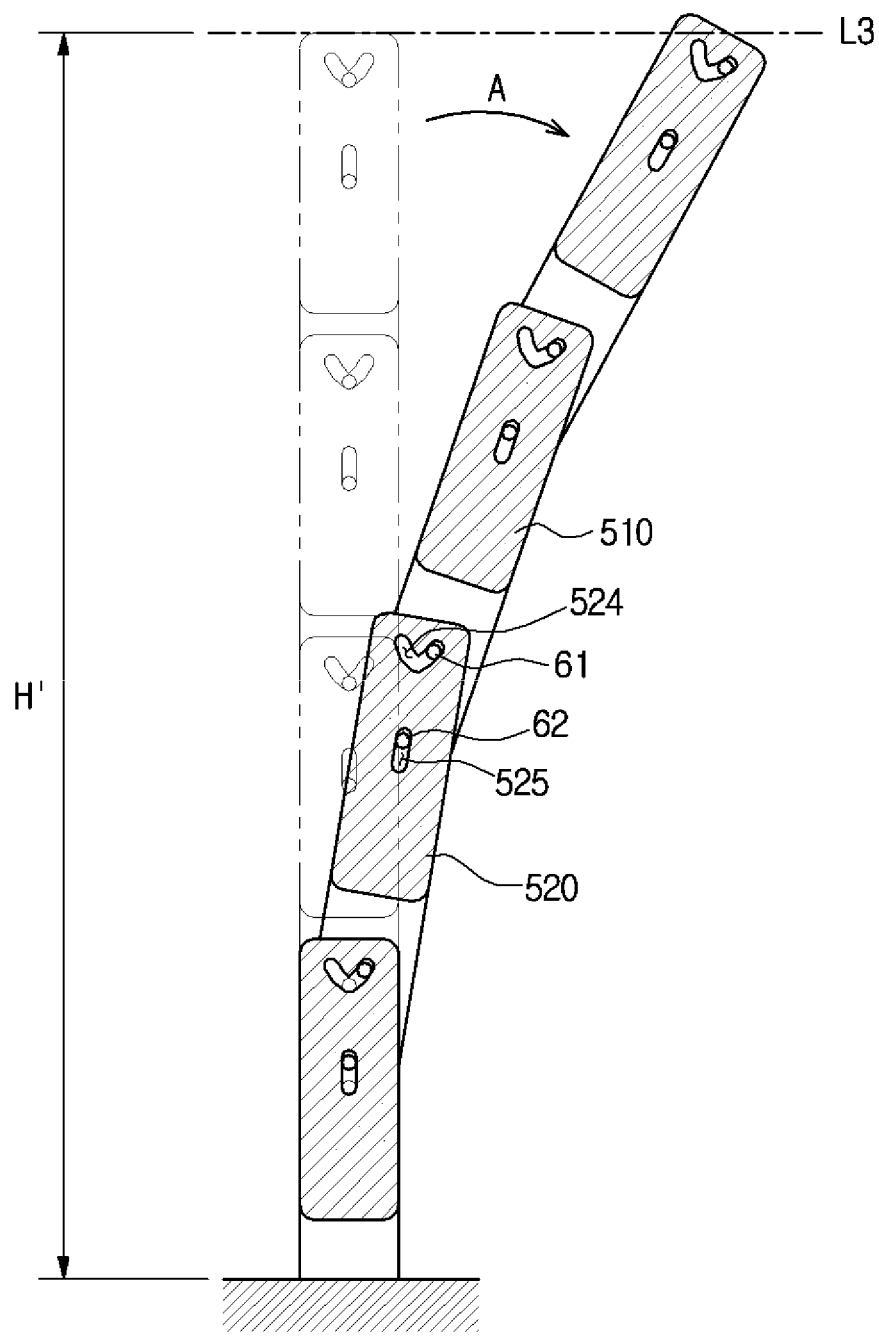
FIG. 11 is a view of a multi-link structure of the walking assistance robot including portion I' of FIG. 5.

FIGS. 9 and 10 are views of positions of pins according to an operation of the link illustrated in FIG. 6, and FIG. 11 is a view of a multi-link structure of the walking assistance robot including portion I' of FIG. 5.

Referring to FIGS. 9 and 10, when a link that constitutes the frame 51 of the walking assistance robot 50 is pivoted, the pins 61 and 62 may be moved along the first slot 524 and the second slot 525 so that the entire heights H1 and H2 of the link assembly before and after the link is pivoted, respectively, remain the same. For example, even when the link that constitutes the frame 51 of the walking assistance robot 50 is pivoted, the entire H1 before pivoting and the height H2 after pivoting of the link assembly may be maintained.

If, in an initial state (see FIG. 9) in which the first pin 61 is disposed at the lowest point of the first slot 524 and the second pin 62 is disposed at the lowest point of the second slot 525, the first link 510 is pivoted in a direction A (see FIG. 10), the first pin 61 may slide along the first slot 524 in a curve direction S1 that is parallel to the direction A. In this case, the second pin 62 may slide along the second slot 525 in an upward direction S2. As a result, the first link 510 may be rotated in the direction A and may ascend in an upward direction. A height l1 at which the first pin 61 ascends along the first slot 524, may be equal to a height l2 at which the second pin 62 ascends along the second slot 525.

While the first link 510 moves in the upward direction, the link assembly is also pivoted, and, therefore, while the length of the link assembly increases, the height of the link assembly remains the same. For example, shapes and sizes of the pins 61 and 62 and the slots 524 and 525 are set so that a height H1 of a coupling body of the first link 510 and the second link 520 before the first link 510 is pivoted, may be maintained to be the same as a height H2 of a coupling body of the first link 510 and the second link 520 after the first link 510 is pivoted.

If the first link 510 is pivoted, the first pin 61 may be supported by an inner surface of the first slot 524, and the second pin 62 may be supported by an inner surface of the second slot 525. The first pin 61 is supported by the inner surface of the first slot 524 so that the first pin 61 can withstand a compressive force applied to the link assembly in the vertical direction, and the second pin 62 is supported by the inner surface of the second slot 525 so that additional rotation of the link assembly can be prevented. Supporting the second pin 62 by the inner surface of the second slot 525 may correspond to supporting the wedge 20a of the upper link 203 by t3 of the lower link 204, as illustrated in FIG. 3. Similarly, the first pin 61 is supported by the inner surface of the first slot 524 so that withstanding of the first pin 61 of the compressive force applied to the link assembly in the vertical direction may correspond to supporting the upper link 203 by t2 of the lower link 204 illustrated in FIG. 3.

Even in the multi-link assembly configured of a plurality of link assemblies connected to one another, as illustrated in FIG. 11, if multi-links are bent in the direction A, a pin disposed on one link along a slot disposed in another adjacent link and may be moved in an upward direction. Although the entire length of the multi-link assembly is increased, the entire height H' from the ground of the multi-link assembly may not change. For example, a top end of the multi-link assembly may be moved on a straight line L3 that is parallel to the ground so that the height H' from the ground of the multi-link assembly may be maintained to be the same when the multi-links are pivoted.

Since the first pin of the link assembly that constitutes the frame is supported by the inner sidewall of the first slot in the form of a downwardly-concave curve, even though the user's load is applied to the frame when the user wears the walking assistance robot, the user's load may be stably supported by the frame. Also, since the second pin of the link assembly is supported by the inner sidewall of the second slot, even though a compressive load is applied to the frame, the frame can be prevented from buckling.

Figure 12:
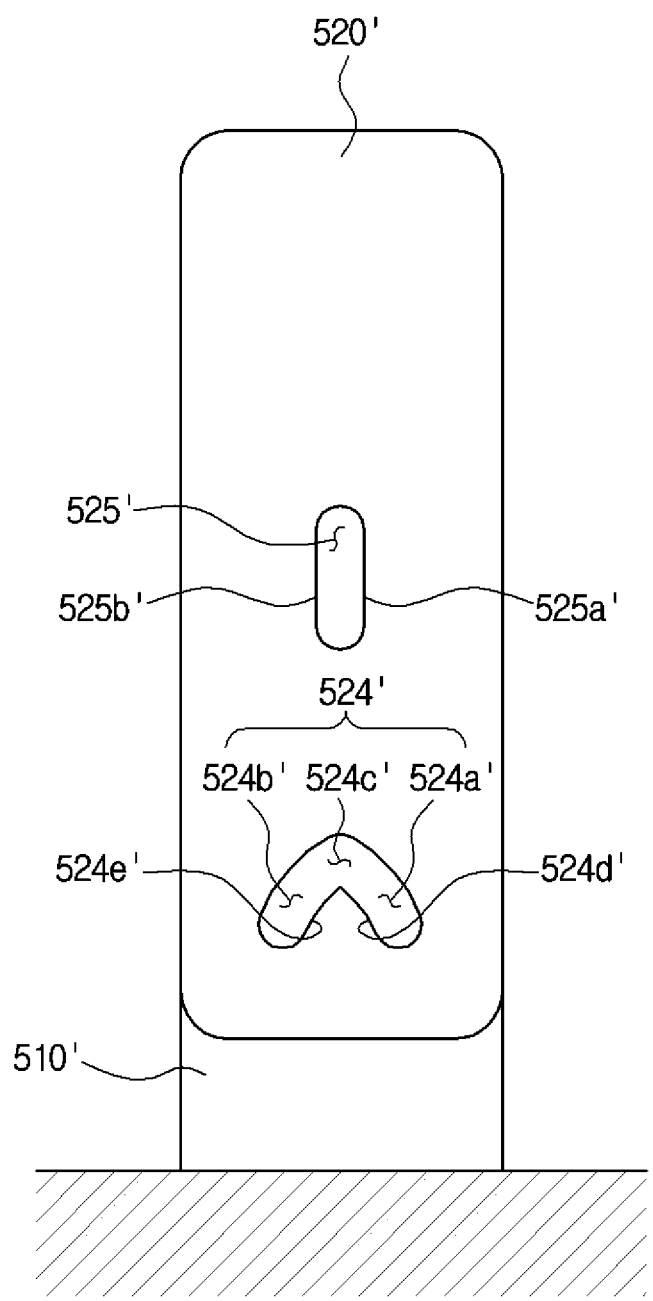
FIG. 12 is a view of a first coupling portion of portion 1" of FIG. 5.
Figure 13:
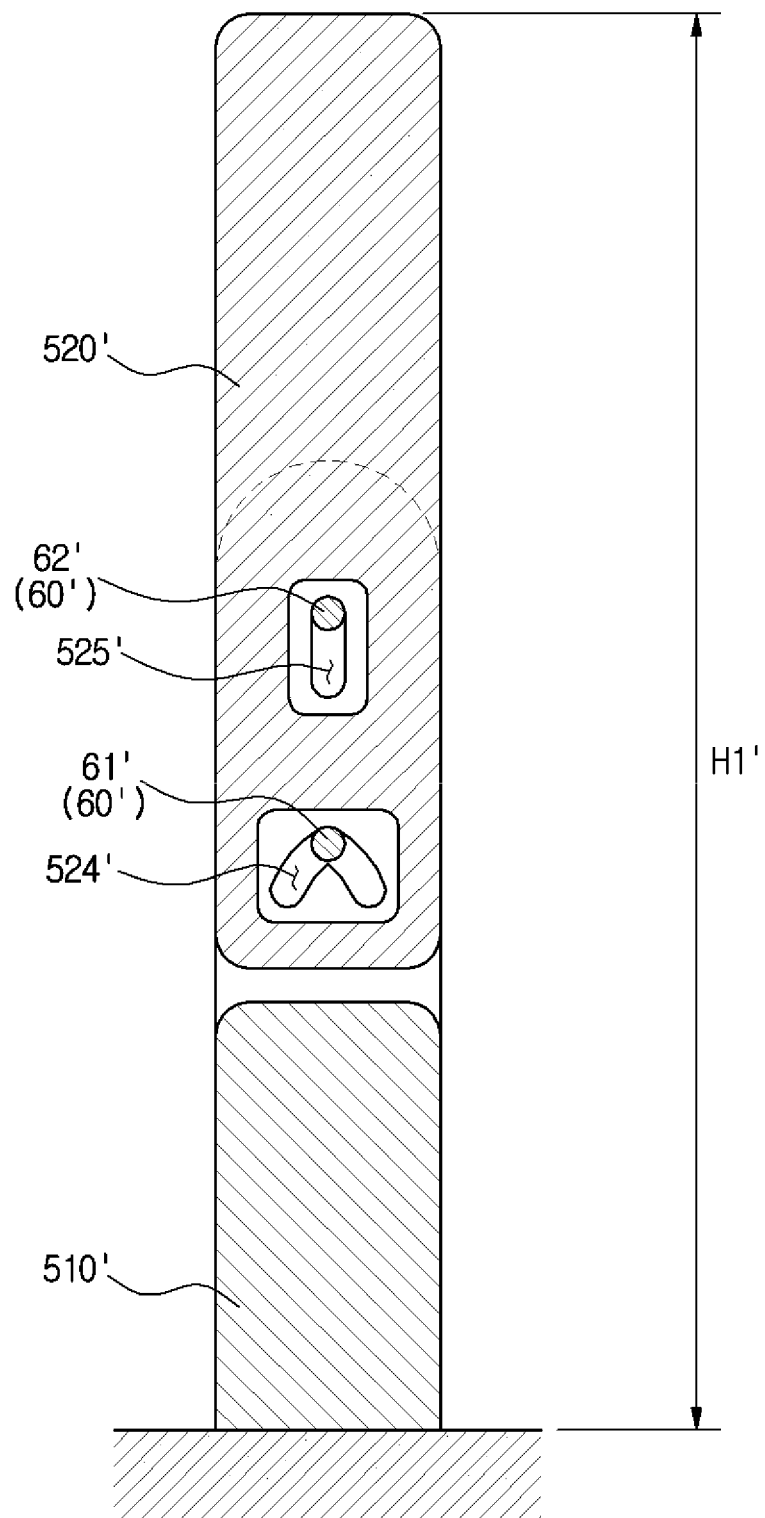
FIGS. 13 and 14 are views of an operation of a link assembly of FIG. 12.
Figure 14:
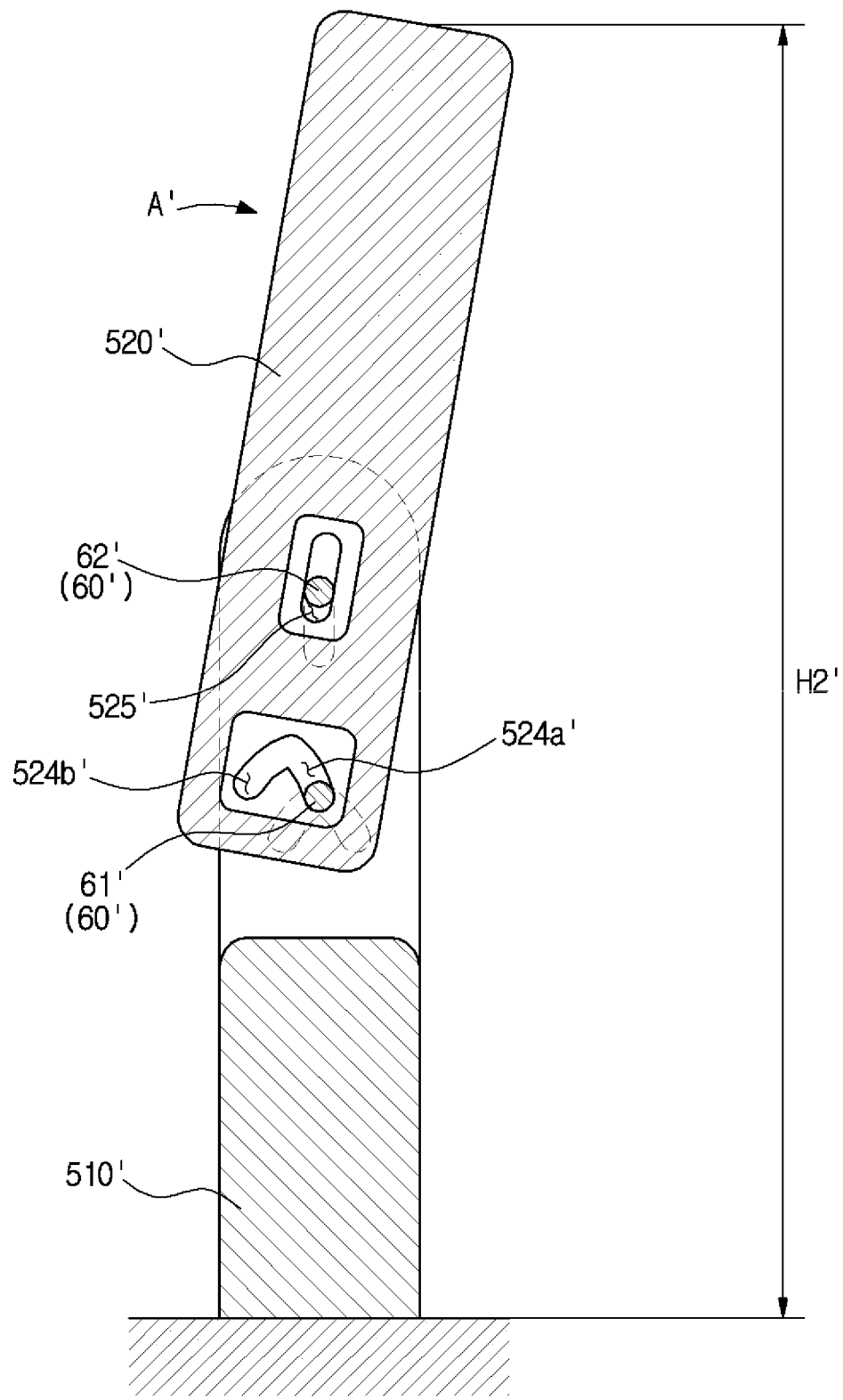
Figure 15:
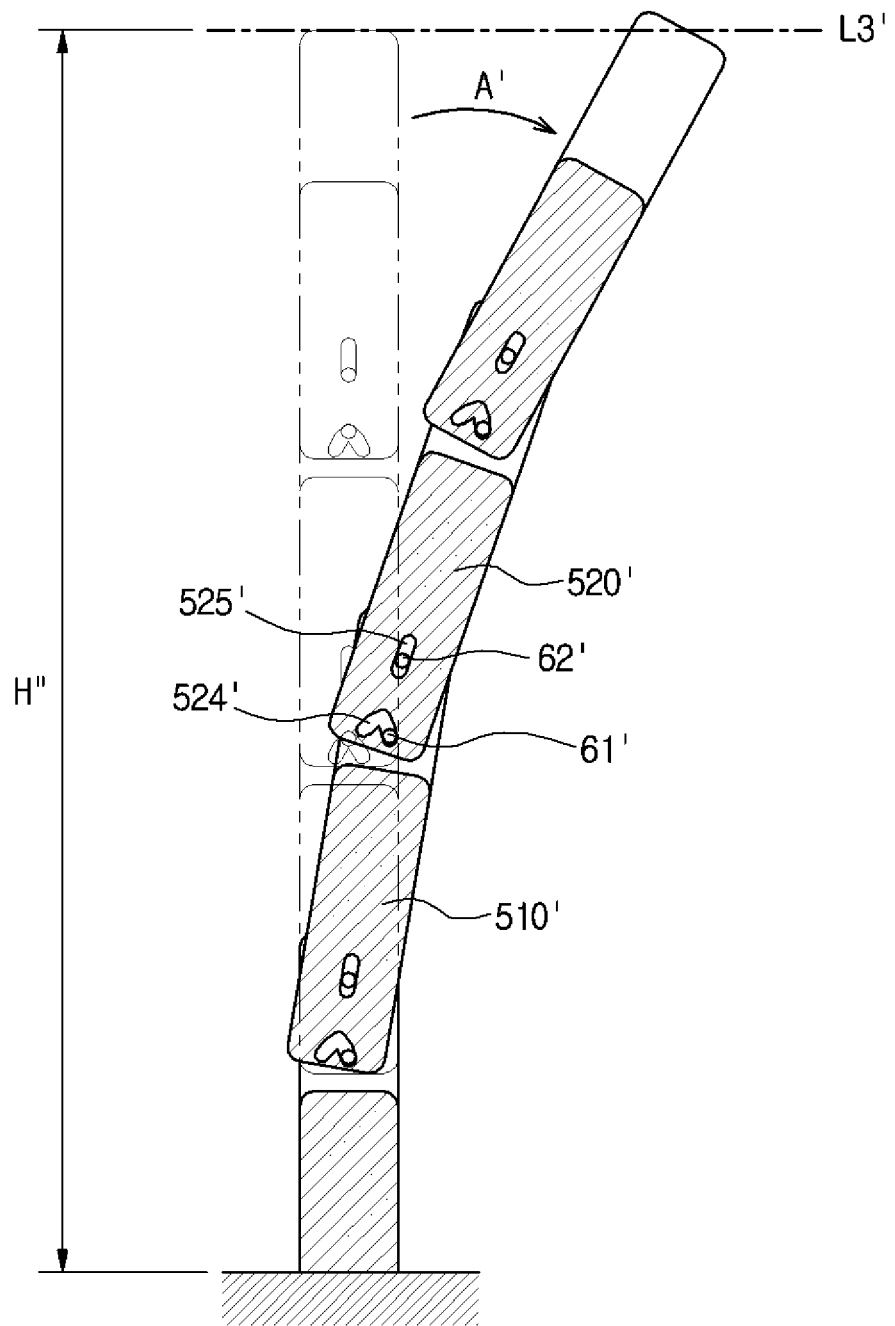
FIG. 15 is a view of a multi-link structure of the walking assistance robot including 1" of FIG. 5.

FIG. 12 is a view of a first coupling portion of portion I'' of FIG. 5, and FIGS. 13 and 14 are views of an operation of a link assembly of FIG. 12, and FIG. 15 is a view of a multi-link structure of the walking assistance robot including I'' of FIG. 5.

Referring to FIGS. 12 through 15, the vertical direction of the link assembly disposed at the portion I'' of FIG. 5 may be reverse with the vertical direction of the link assembly disposed at the portion I' of FIG. 5. If a second link 520' is pivoted with respect to a first link 510' in one direction, the second link 520' may simultaneously make a pivoting motion in one direction and a linear motion in the vertical direction.

The first link 510' and the second link 520' may be connected to each other by a pin 60'. The pin 60' includes a first pin 61' and a second pin 62'. The first pin 61' may be inserted into a first slot 524' formed in the second link 520', and the second pin 62' may be inserted into a second slot 525'. The first slot 524' may be spaced apart from the second slot 525' and may be disposed below the second slot 525'. The second slot 525' may be provided in the form of a straight line that extends in the vertical direction. A right inner surface of the second slot 525' may be referred to as a first support wall 525a', and a left inner surface of the second slot 525' may be referred to as a second support wall 525b'.

The first slot 524' includes extension portions 524a' and 524b' that extend from a mounting portion 524c' based on a straight line that extends in a first direction. The extension portions 524a' and 524b' may extend from the left or right side of the mounting portion 524c' to be tilted in a downward direction. An extension portion disposed on the right side of the mounting portion 524c' may be referred to as the first extension portion 524a', and an extension portion disposed on the left side of the mounting portion 524c' may be referred to as the second extension portion 524b', and an inner sidewall of the first extension portion 524a' may be referred to as a first guide wall 524d', and an inner sidewall of the second extension portion 524b' may be referred to as a second guide wall 524e'. The first slot 524' may be disposed in the form of a curve in which the mounting portion 524c' is set to a highest point.

Hereinafter, an embodiment in which the first slot 524' is disposed in the form of a curve in which the mounting portion 524c' is set to the highest point and the second slot 525' extends in the vertical direction and is disposed above the first slot 524', will be described.

If the second link 520' is pivoted with respect to the first link 510' in one direction, a pivoting motion of the second link 520' may be guided by pins 61' and 62' inserted into the slots 524' and 525'. The pins 61' and 62' are fixed to the first link 510' and are not moved even though the second link 520' is pivoted, and the slots 524' and 525' may be moved together with the second link 520'. The slots 524' and 525' may be guided by the pins 61' and 62' so that the second link 520' may simultaneously make a pivoting motion in one direction and a motion in the vertical direction.

As illustrated in FIG. 13, when the first link 510' and the second link 520' extend in the vertical direction, the first pin 61' may be disposed at the mounting portion 524c' that is a highest point of the first slot 524', and the second pin 62' may be disposed at a highest point of the second slot 525'.

As illustrated in FIG. 14, if the second link 520' is pivoted in a direction A', the first slot 524' may be pivoted in the direction A' and may be moved in an upward direction so that the first pin 61' may be disposed at the first extension portion 524a', and the second slot 525' may be moved in the upward direction so that the second pin 62' may be disposed at a lower portion of the second slot 525'. After the second link 520' is pivoted in the direction A', the first pin 61' and the second pin 62' may be disposed at non-highest points of the first slot 524' and the second slot 525'. The second link 520' may be maintained in a pivoted state in such a way that the inner surface 524d' of the first extension portion 524a' is supported by the first pin 61' and the second support wall 525b' that is a left inner surface of the second slot 525' is supported by the second pin 62', and even though a compressive load is applied to the link assembly, the link assembly can be prevented from buckling.

As the second link 520' is pivoted, the first slot 524' and the second 525' are moved in the upward direction with respect to the first pin 61' and the second pin 62'. Thus, a length from a particular point of the first link 510' or the ground to a top end of the second link 520' may be increased. However, since the second link 520' is pivoted with respect to the first link 510', a length H2' from the ground to the top end of the second link 520' after the second link 520' is pivoted, may not be greater than a length H1' from the ground to the top end of the second link 520' before the second link 520' is pivoted. For example, even though the second link 520' is pivoted with respect to the first link 510', the top end of the second link 520' may be moved along the downwardly-concave curve so that the entire height of the link assembly may be increased, or the top end of the second link 520' may be moved along a straight line that is parallel to a bottom surface of the second link 520' so that the entire height of the link assembly may be the same before and after pivoting is performed.

As illustrated in FIG. 15, even in a multi-link assembly configured of a plurality of link assemblies connected to one another, if multi-links are bent in the direction A', one link may be moved upwardly with respect to a pin mounted on a link disposed at a lower position. Thus, the length of the multi-link assembly before and after pivoting is performed, may be increased, and the height H" of the multi-link assembly from the ground may not change. For example, when the multi-link assembly is pivoted, a top end of the multi-link assembly may be moved in a straight line L3' that is parallel to the ground. Since an inner surface of a slot formed in one link is supported by a pin inserted into a slot disposed at a lower position, even though the compressive load is applied to the multi-link assembly, the link assembly may not be buckled.

Figure 16:
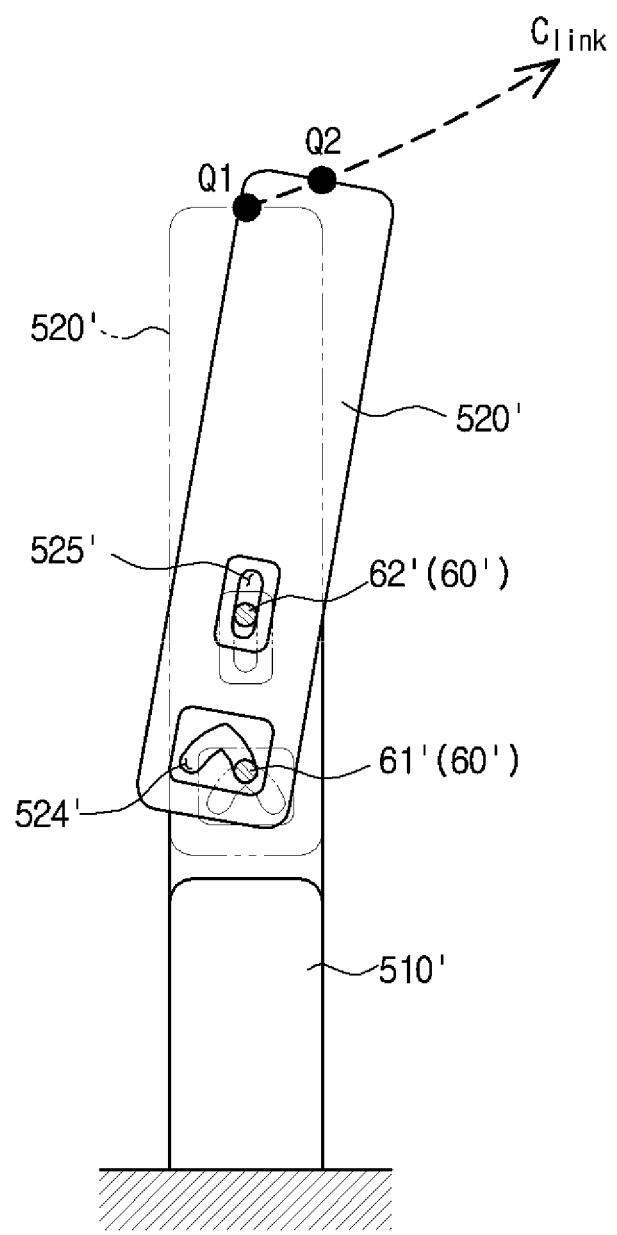
FIGS. 16 and 17 are views for conceptually describing the relationship between an angle of a link when the link included in portion 1" of FIG. 5 is pivoted, and a length of the link assembly.
Figure 17:
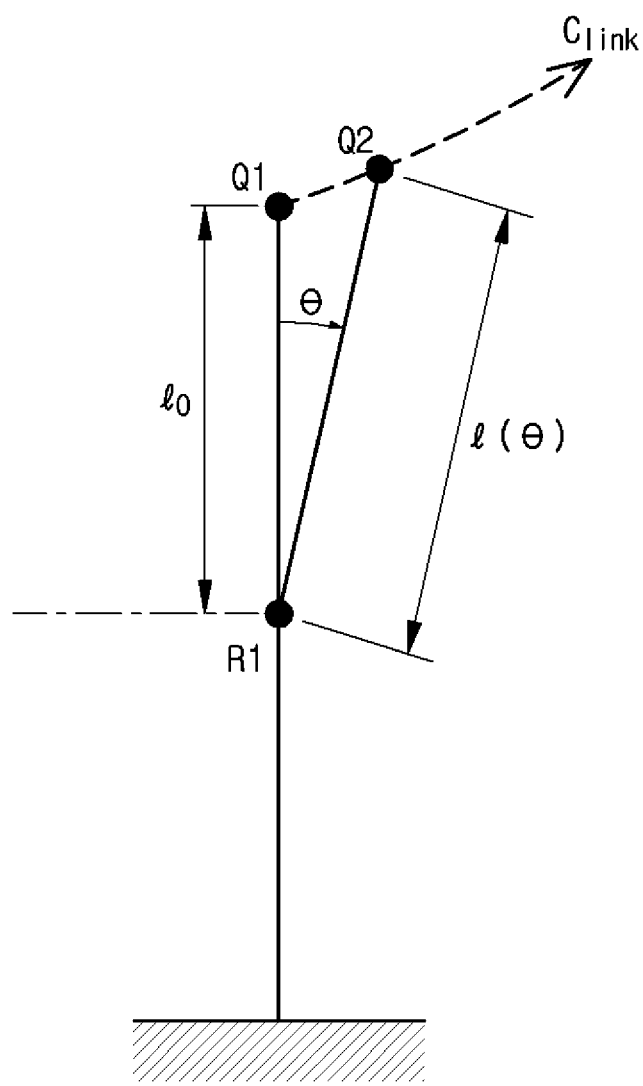

FIGS. 16 and 17 are views for conceptually describing the relationship between an angle of a link when the link included in portion 1" of FIG. 5 is pivoted, and a length of the link assembly.

Referring to FIGS. 16 and 17, when the first pin 61' and the second pin 62' are fixed to the first link 510' and the first slot 524' and the second slot 525' are formed in the second link 520', if the second link 520' is pivoted with respect to the first link 510', the first slot 524' and the second slot 525' are moved in a configuration in which the first pin 61' and the second pin 62' are fixed to the first link 510', so that the position of the first pin 61' within the first slot 524' and the position of the second pin 62' within the second slot 525' may change.

If it is assumed that, before the second link 520' is pivoted with respect to the first link 510', the first pin 61' is disposed at the highest point of the first slot 524' and the second pin 62' is disposed at the highest point of the second slot 525', as the second link 520' is pivoted with respect to the first link 510', the first slot 524' and the second slot 525' may be moved together with the second link 520', and the first pin 61' and the second pin 62' may be disposed at other points that are not the highest points of the first slot 524' and the second slot 525'. Since the first pin 61' and the second pin 62' are fixed to the first link 510', if the first pin 61' and the second pin 62' are disposed at other points that are not the highest points of the first slot 524' and the second slot 525', the height of the top end of the second link 520' is increased so that the length of the first link 510' and the second link 520' may increase. For example, the length of the first link 510' and the second link 520' may be increased by a distance at which the second pin 62' is moved within the second slot 525'.

Referring to FIG. 17, a position of the second pin 62' that connects the first link 510' and the second link 520' before the second link 520' is pivoted with respect to the first link 510' is referred to as R1. A length from R1 to the top end of the second link 520' may be l0. After the second link 520' is pivoted with respect to the first link 510', a length from R1 to the top end of the second link 520' may be l($\theta$).

If the second link 520' is pivoted with respect to the first link 510', the height of the top end of the second link 520' may be increased. For example, as illustrated in FIG. 16, as the second link 520' is pivoted, the top end of the second link 520' may be moved along a curve Clink having a lowest point. If the position of the top end of the second link 520' before pivoting is performed, is Q1 and the position of the top end of the second link 520' after pivoting is performed, is Q2, Q1 and Q2 may be disposed on the curve Clink having the lowest point.

Hereinafter, a method, whereby a shape of the first slot 524' is implemented so that the top end of the second link 520' before and after pivoting is performed, can be moved along the curve Clink having the lowest point, will be described.

In a state in which the first link 510' and the second link 520' extend in one straight line, a distance between the second pin 62' and the top end of the second link 520' is l0. After the second link 520' is pivoted at an angle of θ based on R1 that is the position of the second pin 62' before the second link 520' is pivoted, a distance between the position R1 of the second pin 62' and the top end of the second link 520' may be l(θ). In this case, a variation Δl(θ) in a distance between R1 and top ends of the first link 510' and the second link 520' may be defined by Equation 1 below.

$$\Delta l(\theta) = l(\theta) - l0 \quad \text{Equation 1}$$

In Equation 1, Δl(θ) may be the variation in the length of the link assembly in which the first link 510' and the second link 520' are connected to each other due to the pivoting thereof by the angle θ.

Hereinafter, a shape of the first slot 524' when a function regarding Δl(θ) is given, will be found.

Figure 18:
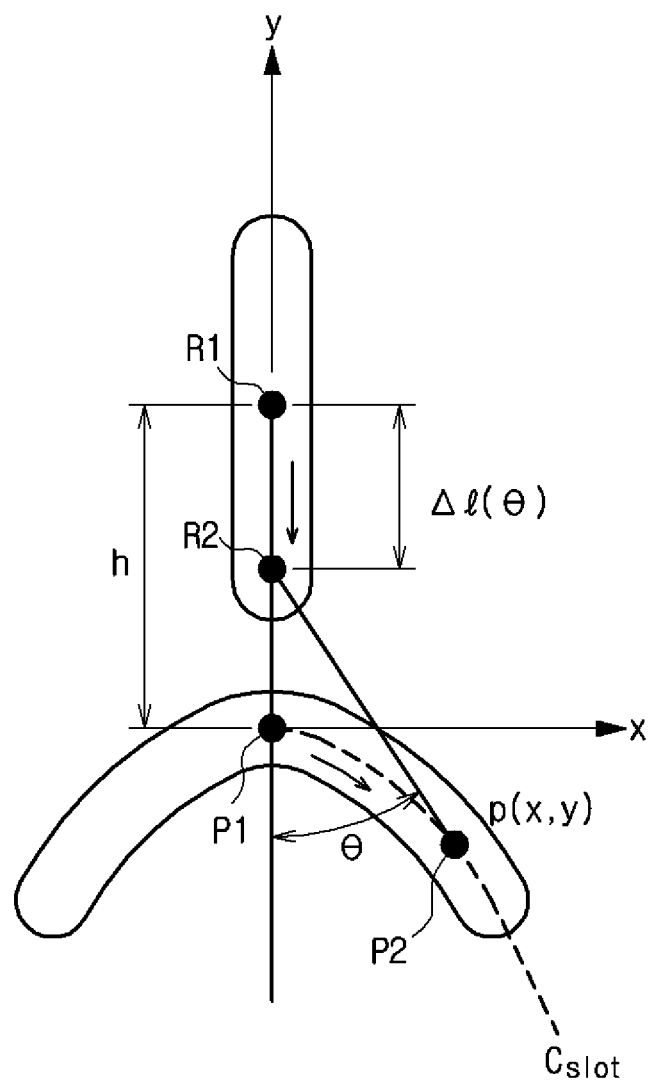
FIG. 18 is a view for describing the relationship of positions of pins that change within a slot as the link disposed in portion 1" of the walking assistance robot of FIG. 5 is rotated.

FIG. 18 is a view for describing the relationship of positions of pins that change within a slot as the link disposed in portion l'' of the walking assistance robot of FIG. 5 is rotated.

If the second link 520' is pivoted with respect to the first link 510', the first slot 524' and the second slot 525' associated with the second link 520' move together with the second link 520' so that positions of the first pin 61' and the second pin 62' within the first slot 524' and the second slot 525' change. Alternatively, if the first link 510' pivots with respect to the second link 520', the first slot 524' and the second slot 525' may remain fixed and the first pin 61' and the second pin 62' may move within the first slot 524' and the second slot 525'.

Referring to FIG. 18, in an initial state before the link assembly is pivoted, the position of the second pin 62' may be R1, and the position of the first pin 61' may be P1. Before the second link 520' is pivoted, a distance between the first pin 61' and the second pin 62' may be h.

After the link assembly is pivoted at a desired (or, alternatively, a predetermined) angle, the position of the second pin 62' may be R2, and the position of the first pin 61' may be P2. If it is assumed that there is x-y coordinates in which the position P1 of the first pin 61' before pivoting is performed is set to the origin, the position P2 of the first pin 61' after pivoting is performed may be p(x,y) in the x-y coordinates. A length at which the second pin 62' is moved within the second slot 525' after pivoting is performed, is equal to the variation Δl(θ) in the entire length of the first link 510' and the second link 520' before and after pivoting is performed.

The function p(x,y) that is the position of the first pin 61' and has x-y coordinates defined by Equation 2.

$$x = h \sin \theta$$

$$y = h - \Delta l(\theta) - h \cos \theta \quad \text{Equation 2}$$

If θ is erased from the above two equations, then Equation 2 becomes Equation 3 below.

$$y = h - \Delta l(\theta) - h\cos\theta \quad \text{Equation 3}$$
$$= h - \Delta l(\theta) - \sqrt{h^2 - x^2}$$
$$= h - \sqrt{h^2 - x^2} - \Delta l\left(\operatorname{asin}\frac{x}{h}\right)$$

When the function regarding Δl(θ) is given, the shape of the first slot 524' may be defined by Equation 4.

$$y = h - \sqrt{h^2 - x^2} - \Delta l\left(\operatorname{asin}\frac{x}{h}\right) \quad \text{Equation 4}$$

The first slot 524' may be formed to satisfy Equation 4 on the x-y coordinates, and the second slot 525' may be formed to extend in the y-axis direction.

When the first slot 524' and the second slot 525' are formed in the second link 520', as described above, if the second link 520' is pivoted with respect to the first link 510', the length of the first link 510' and the second link 520' may increase, and top ends Q1 and Q2 of the second link 520' may move along the downwardly-concave curve $C_{link}$.

For example, if $C_{link}$ is a straight line that is horizontal with respect to the ground, Δl(θ) may be obtained by Equation 5 below.

$$\Delta l(\theta) = \frac{l_o}{\cos\theta} - l_o \quad \text{Equation 5}$$

If Δl(θ) in Equation 5 is substituted into Equation 4, Equation 6 may be established.

$$y = h - \sqrt{h^2 - x^2} - \frac{hl_o}{\sqrt{h^2 - x^2}} + l_o \quad \text{Equation 6}$$

Using Equation 6, a y-value may be obtained based on the distance between the first pin 61' and the second pin 62' h, x, and the distance between the second pin 62' and the top end of the second link 520' $l_o$.

If the first slot 524' is formed to satisfy Equation 6, the top end of the second link 520' may move along the straight line that is horizontal with respect to the ground, so that the height of the link assembly before and after pivoting is performed is constant.

Figure 19:
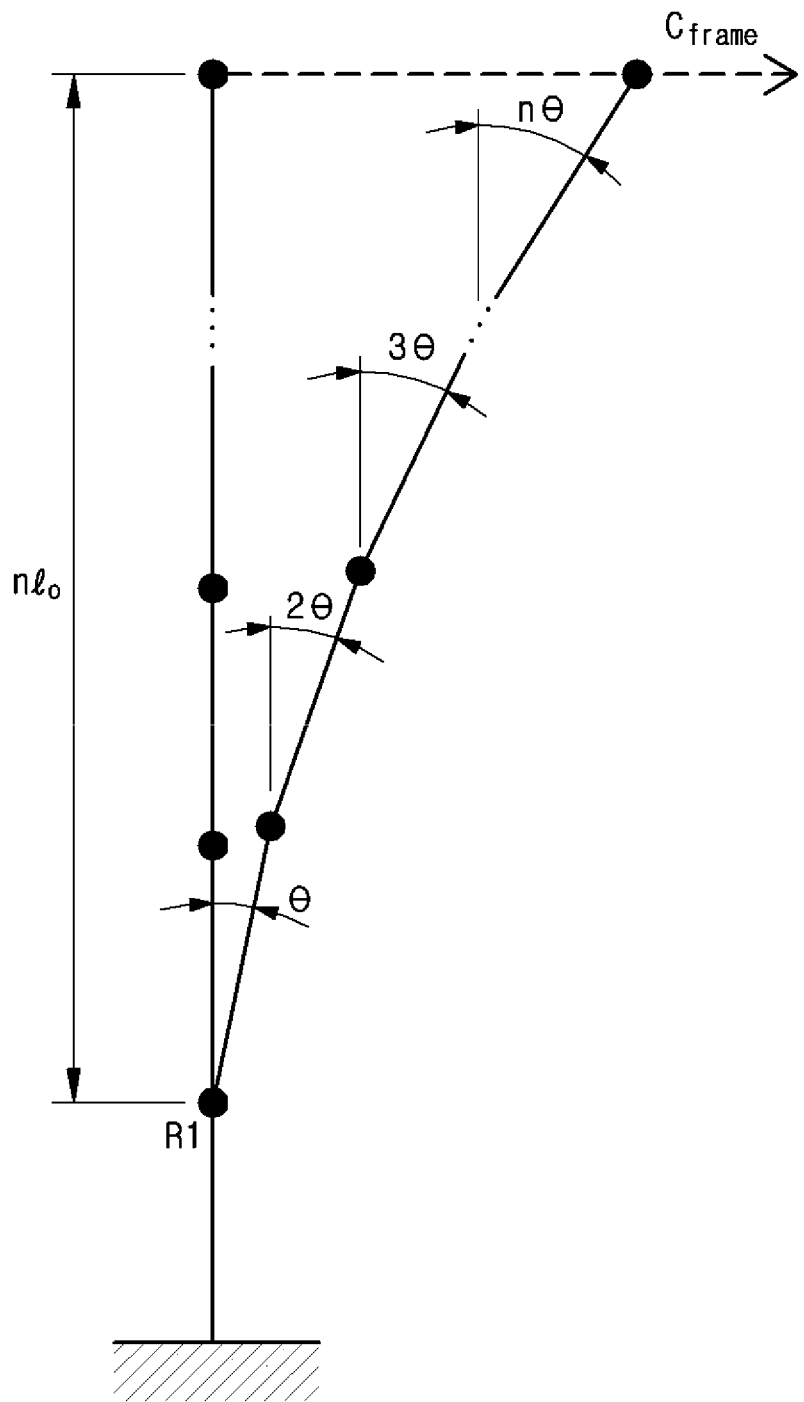
FIG. 19 is a view for describing rotation angles of a plurality of links disposed in portion 1" of the walking assistance robot of FIG. 5.

FIG. 19 is a view for describing rotation angles of a plurality of links disposed in portion l'' of the walking assistance robot of FIG. 5.

Referring to FIG. 19, the frame 51 disposed on the walking assistance robot 50 may be configured of n links that are pivotally connected to one another. The frame 51 may have a structure in which link assemblies including the first link 510' and the second link 520' disposed above the first link 510' are continuously connected to one another. One link may be pivoted to be rotated at an angle θ with respect to another adjacent link connected to a lower portion of the one link. If it is assumed that the height of the frame 51 is maintained before and after pivoting and a particular position of the frame 51 is moved in a straight line $C_{frame}$ that is parallel to the ground, the Equation 7 may be obtained.

$$nl_0 = l(\theta)\cos\theta + l(\theta)\cos2\theta + l(\theta)\cos3\theta + \ldots + l(\theta)\cos n\theta \quad \text{Equation 7}$$

$$l(\theta) = \frac{nl_0}{\cos\theta + \cos2\theta + \cos3\theta + \ldots + \cos n\theta}$$

Using Equation 7, $\Delta l(\theta)$ may be obtained by Equation 8.

$$\Delta l(\theta) = \frac{n}{\sum_{k=1}^{n}\cos k\theta}l_0 - l_0 \quad \text{Equation 8}$$

If $\Delta l(\theta)$ is substituted into equation 4, Equation 9 may be established.

$$y = h - \sqrt{h^2 - x^2} - \frac{n}{\sum_{k=1}^{n}\cos k\left(\operatorname{asin}\frac{x}{h}\right)}l_0 + l_0 \quad \text{Equation 9}$$

Using Equation 9, a y-value may be obtained based on the distance between the first pin 61' and the second pin 62' h, x, and the distance between the second pin 62' and the top end of the second link 520 l0 obtained.

If the first slot is formed to satisfy Equation 9, the height of the frame 51 may be maintained before and after pivoting, and the particular point of the frame 51 may be moved in a straight line Cframe that is parallel to the ground.

Thus, a first slot equation may be established in the x-y coordinates, and the first slot may be formed to correspond to the position of the first pin. By using Equation 9, the shape of the first slot in the form of a curve formed in a plurality of links that constitutes the frame may be determined.

As described above, the frame of the walking assistance robot is configured of the plurality of links that are pivotally connected to one another, so that the frame is bent according to a change in the curve of the body and the frame can be in close contact with the body and the sense of wearing of the walking assistance robot can be improved.

The links that constitute the frame may be disposed so that their length may change before and after pivoting is performed. Thus, the height of the particular point of the frame may be maintained before and after pivoting is performed. Pins that connect the plurality of links are configured to be inserted into and to slide in a curve-shaped slot and a slot in the vertical direction so that, if the frame is bent, the links may simultaneously make a pivoting motion and a motion in a lengthwise direction in which the links are connected to one another, so that the entire length of the frame can be increased. Thus, ends of the frame may be moved along the straight line that is horizontal with respect to the ground. Even when the frame is bent, the height of the frame does not change, and the user who wears the walking assistance robot can walk comfortably.

The first pin is supported by the inner surface of the first slot having the curve shape so that the user's load can be stably supported, and the second pin is supported by the inner surface of the second slot that extends in the vertical direction so that, even when the compressive load is applied to the frame, the frame can be prevented from buckling.

Through this configuration, the walking assistance robot is disposed to be in close contact with the body so that the walking assistance robot can be slim to be worn under clothes and repulsion for the exterior of the walking assistance robot can be eliminated.

As described above, in a link assembly, a frame, and a walking assistance robot having the same according to the one or more example embodiments, the link assembly, the frame, and the walking assistance robot are flexibly in close contact with a user's body so that a sense of wearing can be improved and the user's load can be stably supported.

Although a few example embodiments have been shown and described, it would be appreciated by those skilled in the art that changes may be made in these example embodiments without departing from the principles and spirit thereof, the scope of which is defined in the claims and their equivalents.

Figure 20:
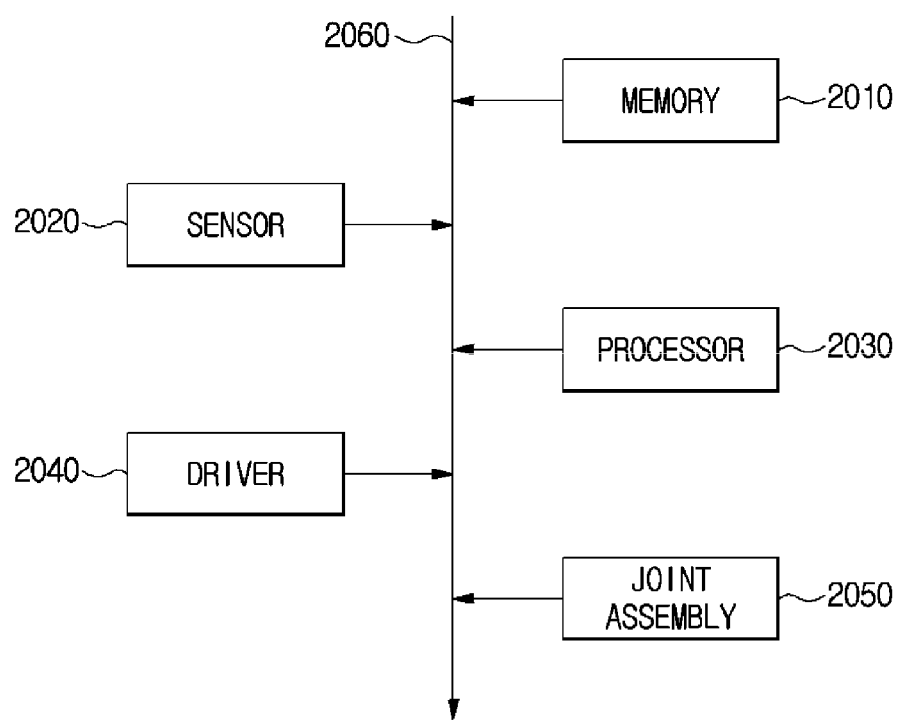
FIG. 20 illustrates a walking assistance robot according to some example embodiments.

FIG. 20 illustrates a walking assistance robot according to some example embodiments.

As illustrated in FIG. 20, a walking assistance robot may include, for example, a memory 2010, a sensor 2020, a processor 2030, a driver 2040, a joint assembly 2050 that may send data to and/or receive data from one another using a data bus 2060.

The memory 2010 may be any device capable of storing data. For example, the memory may be a non-volatile memory, a volatile memory, a hard disk, an optical disk, and a combination of two or more of the above-mentioned devices. The memory may be a non-transitory computer readable medium. The non-transitory computer-readable media may also be a distributed network, so that the program instructions are stored and executed in a distributed fashion. The non-volatile memory may be a Read Only Memory (ROM), a Programmable Read Only Memory (PROM), an Erasable Programmable Read Only Memory (EPROM), or a flash memory. The volatile memory may be a Random Access Memory (RAM).

The sensor 2020 may be configured to sense whether the user is walking. For example, the sensor 2020 may be a pressure sensor. The pressure sensor may be a ground reaction force (GRF) sensor that senses GRF transferred to the user's foot when the user walks.

The processor 2030 may be any device capable of processing data including, for example, a microprocessor configured to carry out specific operations by performing arithmetical, logical, and input/output operations based on input data, or capable of executing instructions included in computer readable code. The processor 2030 may be a logic chip, for example, a central processing unit (CPU), a controller, or an application-specific integrated circuit (ASIC), that when, executing the instructions stored in the memory 2010, configures the processor 2030 as a special purpose machine such that the processor 2030 is configured to determine an amount of tension to utilize to pull the wires associated with the joint assembly 2030 based on a result of sensing performed by the sensor 2030, and instruct the driver 2040 to pull the wires with the determined tension.

The processor 2030 may control the amount of tension provided to the wires by the driver 2040 based on a weight of a wearer of the walking assistance robot. For example, the processor 2030 may measure a weight of the wearer using the pressure sensor 2020 installed at one or more of the foot structures, and adjust the amount of torque based on the sensed weight. The sensed weight may include an object that the wearer is holding.

Further still, the processor 2030 may provide a different amount of torque to the joint assembly 2050 as the wearer moves through various phases of a walking cycle. For example, the processor 2030 may instruct the walking assistance robot to increase the torque, if the joint assembly 2050 is exerting positive work on the leg, for example, when the wearer is increasing a pace of walking on a flat surface, a sloped surface or a stepped surface. Likewise, the processor 2030 may instruct the walking assistance robot to increase a damping torque applied to a leg of the wearer, if the joint assembly 2050 is exerting negative work on the leg, for example, when the wearer is decreasing a pace of walking on the flat surface, the sloped surface or the stepped surface.

The driver 2040 may be a motor that generates torque according to electric energy supplied from a power supply (not shown). The motor may be provided with an encoder. Alternatively, the driver 2040 may include at least one piston or cylinder device that is operated by electric energy or by fluidic pressure such as, for example, hydraulic pressure or pneumatic pressure generating torque. The driver 2040 may exert an amount of torque based on instructions received from the processor 2030.

The joint assembly 2050 may include wires and pulleys that move in response to the torque applied to the cables by the driver 2040 such that the joint assembly 2050. The joint assembly 2050 may also include one or more frames that each include a plurality of links that are in the form of wedges and corresponding groves and/or include a curved slot and a corresponding straight slot that confine an amount of linear and rotational motion of the links.

The frames may move in response to torque applied to the joints connected thereto to assist the wearer with walking. Due to the plurality of links, when the user wears the walking assistance robot 1, the walking assistance robot 1 corresponds to a shape of the user's body that contacts the walking assistance robot 1 and thus the first frame and the second frame can be flexibly bent. Further, if the frames bend, the links may simultaneously make a pivoting motion and a motion in a lengthwise direction in which the links are connected to one another, so that the length of the frame can be increased such that, when the frame is bent, the height of the frame does not change, and the user can walk comfortably.

What is claimed is:

1. A link assembly configured to perform a rotary motion and a linear motion in response to a force applied to the link assembly, the link assembly comprising:
   pins including a pivoting pin and a supporting pin;
   a first link configured to have the pins inserted therethrough; and
   a second link connected to the first link, the second link including a first coupling portion having a first guide and a second guide formed therein, the first guide corresponding to the pivoting pin, the first guide configured to guide the first link in the rotary motion and the linear motion with respect to the second link, and the second guide corresponding to the supporting pin, the second guide configured to limit the rotary motion of the supporting pin such that the first link is supported by the second link.

2. The link assembly of claim 1, wherein the first guide comprises:
   a first guide wall configured to support the pivoting pin when one or more of the first link and the second link rotate.

3. The link assembly of claim 1, wherein the second guide comprises:
   a supporting wall extending in a direction of the linear motion, the supporting wall configured to support the supporting pin when the first link rotates such that the second guide limits the rotary motion.

4. The link assembly of claim 1, wherein the first guide comprises:
   a mounting portion configured to support the pivoting pin if the first link and the second link are aligned in a direction of the linear motion, and
   an extension portion that extends from the mounting portion, the extension portion including a first guide wall therein.

5. The link assembly of claim 4, wherein the extension portion comprises:
   a first extension portion extending from a first side of the mounting portion and a second extension portion extending from a second side of the mounting portion.

6. The link assembly of claim 5, wherein the first extension portion and the second extension portion are symmetrical about a straight line that passes the mounting portion and extends in the direction of the linear motion.

7. The link assembly of claim 1, wherein the first guide is in a curved shape such that the first guide has an inflection point, the inflection point being a point in which the curved shape of the first guide changes concavity.

8. The link assembly of claim 1, wherein the second guide is spaced apart from the first guide in a direction of the linear motion.

9. The link assembly of claim 1, wherein the second guide extends in a direction of the linear motion such that the second guide is configured to guide the supporting pin in the direction of the linear motion.

10. The link assembly of claim 1, wherein the pivoting pin is spaced apart from the supporting pin in a direction of the linear motion.

11. The link assembly of claim 1, wherein the first link comprises:
    two second coupling portions that face each other with a space therebetween such that the second coupling portions are configured to receive the first coupling portion in the space.

12. The link assembly of claim 11, wherein the first and second coupling portions are configured to receive the pivoting pin and the supporting pin therethrough.

13. The link assembly of claim 1, wherein the first link includes a plurality of first links and the second link includes a plurality of second links such that the plurality of first links and the plurality of second links are alternately connected to one another.

14. A link assembly configured to be worn by a user and to rotate and move linearly in response to a force applied to the link assembly, the link assembly comprising:
    a first pin and a second pin;
    a first link configured to extend along a leg of the user, the first link having a first coupling hole and a second coupling hole extending therethrough, the first coupling hole spaced apart from the second coupling hole, the first coupling hole configured to receive the first pin and the second coupling hole configured to receive the second pin; and
    a second link configured to connect to the first link such that the second link is extendible, the second link having a first slot and a second slot, the first slot configured to receive the first pin and the second slot configured to receive the second pin such that the first slot and the second slot are confined by the first pin and the second pin, respectively, and move so that the first link and the second link rotate and move linearly with respect to each other.

15. The link assembly of claim 14, wherein the first slot and the second slot have different shapes.

16. The link assembly of claim 15, wherein the first slot is in a curved shape, and the second slot is in a straight line.

17. The link assembly of claim 16, wherein the first slot extends about the straight line of the second slot.

18. The link assembly of claim 14, wherein the first slot is a symmetric curve.

19. The link assembly of claim 14, wherein the first slot is in a curved shape such that the first slot has an inflection point, the inflection point being a point in which the curved shape of the first slot changes concavity.

20. A link assembly comprising:
a plurality of alternating links, each of the plurality of links including a first end having a projecting tongue and a second end having a corresponding groove, the projecting tongues and grooves each including traversing bores therethrough, the traversing bores associated with a first one of the projecting tongue and groove include slots, the slots including a curved slot and a straight slot located symmetrical about an inflection point of the curved slot such that the traversing bores allow a limited amount of rotational motion and a limited amount of linear movement between the plurality of links while supporting a compressive force applied therebetween in response to a force applied to the link assembly, the inflection point of the curved slot being a point in which the curved slot changes concavity.

21. The link assembly of claim 20, wherein the traversing bores associated with a second one of the projecting tongue and groove include coupling holes therethrough that correspond to the slots such that corresponding ones of the slots and coupling holes are configured to receive pins therethrough.

22. The link assembly of claim 21, further comprising:
a first pin and a second pin, wherein
the curved slot is configured to receive the first pin and the straight slot is configured to receive the second pin, such that the limited amount of rotational motion between the plurality of links is determined by a shape of the curved slot and the limited amount of linear movement between the plurality of links is determined by a length of the straight slot.

* * * * *